(12) United States Patent
Hufton

(10) Patent No.: US 9,771,415 B2
(45) Date of Patent: Sep. 26, 2017

(54) INFLUENZA VIRUS ANTIBODY COMPOSITIONS

(75) Inventor: Simon Hufton, Hertfordshire (GB)

(73) Assignee: The Secretary of State for Health, London (GB)

(*) Notice: Subject to any disclaimer, the term of this patent is extended or adjusted under 35 U.S.C. 154(b) by 242 days.

(21) Appl. No.: 14/342,376

(22) PCT Filed: Sep. 3, 2012

(86) PCT No.: PCT/GB2012/052164
§ 371 (c)(1),
(2), (4) Date: Jun. 24, 2014

(87) PCT Pub. No.: WO2013/030604
PCT Pub. Date: Mar. 7, 2013

(65) Prior Publication Data
US 2014/0302063 A1    Oct. 9, 2014

(30) Foreign Application Priority Data

Sep. 2, 2011 (GB) .................................. 1115214.7

(51) Int. Cl.
| C07K 16/10 | (2006.01) |
| A61K 39/395 | (2006.01) |
| C07K 16/00 | (2006.01) |
| A61K 39/00 | (2006.01) |
| C07K 16/28 | (2006.01) |

(52) U.S. Cl.
CPC .... C07K 16/1018 (2013.01); *A61K 2039/505* (2013.01); *C07K 2317/22* (2013.01); *C07K 2317/24* (2013.01); *C07K 2317/33* (2013.01); *C07K 2317/565* (2013.01); *C07K 2317/567* (2013.01); *C07K 2317/569* (2013.01); *C07K 2317/92* (2013.01)

(58) Field of Classification Search
CPC .............. C07K 14/005; C07K 16/1018; A61K 31/7115; A61K 38/00; A61K 48/0066
See application file for complete search history.

(56) References Cited

U.S. PATENT DOCUMENTS

| 8,192,927 B2 | 6/2012 | Van Den Brink et al. |
| 2009/0092620 A1 | 4/2009 | Moste et al. |
| 2011/0052565 A1 | 3/2011 | Arbabi-Ghahroudi et al. |

FOREIGN PATENT DOCUMENTS

| WO | WO 92/06204 A1 | 4/1992 |
| WO | WO 2007/052242 A1 | 5/2007 |
| WO | WO2008118487 | * 10/2008 |
| WO | WO 2009/053604 A2 | 4/2009 |
| WO | WO 2010/027818 A2 | 3/2010 |
| WO | WO 2010/027818 A3 | 3/2010 |
| WO | WO 2010/081856 A1 | 7/2010 |
| WO | WO 2010/132604 A2 | 11/2010 |
| WO | WO 2010/138564 A1 | 12/2010 |

OTHER PUBLICATIONS

Paul, "Fv Structure and Diversity in three dimension", Fundamental Immunology, 3rd Edition, 1993, pp. 292-295.*
Rudikoff et al. Proc. Natl. Acad. Sci. USA, 1982, 79(6):1979-1983.*
MacCallum et al., 1996, J. Mol. Biol., 262:732-745.*
Casset et al. (Biochemical and Biophysical Research Communications,2003, 307:198-205.*
Sakabe et al.; "A Cross-Reactive Neutralizing Monoclonal Antibody Protects Mice from H5N1 and Pandemic (H1N1) 2009 Virus Infection"; Anitviral Research; vol. 88 No. 3; Dec. 2010; p. 249-255.
Han et al.; "Structural Basis of Influenza Virus Neutralization" Annals of the New York Academy of Sciences; vol. 1217 No. 1; Jan. 2011; p. 178-190.
Ibanez et al.; "Nanobodies With In Vitro Neutralizing Activity Protect Mice Against H5N1 Influenza Virus Infection"; Journal of Infectious Diseases; vol. 203; Apr. 2011; p. 1063-1072.
Hultberg et al.; "Llama-Derived Single Domain Antibodies to Buid Multivalent, SuperPotent and Broadened Neutralizing Anti-Viral Molecules"; PLos One; vol. 6 Issue 4; Apr. 2011; p. 1-6.
Maass et al.; "Alpaca (*Lama pecos*) as a Convenient Source of Recombinant Camelid Heavy Chain Antibodies"; Journal of Immunological Methods; vol. 324; Jul. 2007; p. 13-25.
Great Britain patent application No. 1115214.7; Search Report; dated Dec. 22, 2011; 4 pages.
International Patent Application No. PCT/GB2012/052164; Int'l Search Report; dated Jan. 28, 2013; 5 pages.
International Patent Application No. PCT/GB2012/052164; Int'l Preliminary Report on Patentability; dated Mar. 4, 2014; 9 pages.

(Continued)

*Primary Examiner* — Janet L Andres
*Assistant Examiner* — Barry A Chestnut
(74) *Attorney, Agent, or Firm* — Baker & Hostetler LLP

(57) ABSTRACT

The present invention relates to unique CDR3 amino acid sequences, and to antibodies comprising said sequences. Also provided are therapeutic applications of said antibodies for use in treating or preventing influenza infection, diagnostic applications of said antibodies for use in detecting influenza virus, potency testing of influenza virus vaccines, and screening applications of said antibodies for use in designing a universal influenza vaccine.

16 Claims, 5 Drawing Sheets

(56) References Cited

OTHER PUBLICATIONS

Figure 1A:
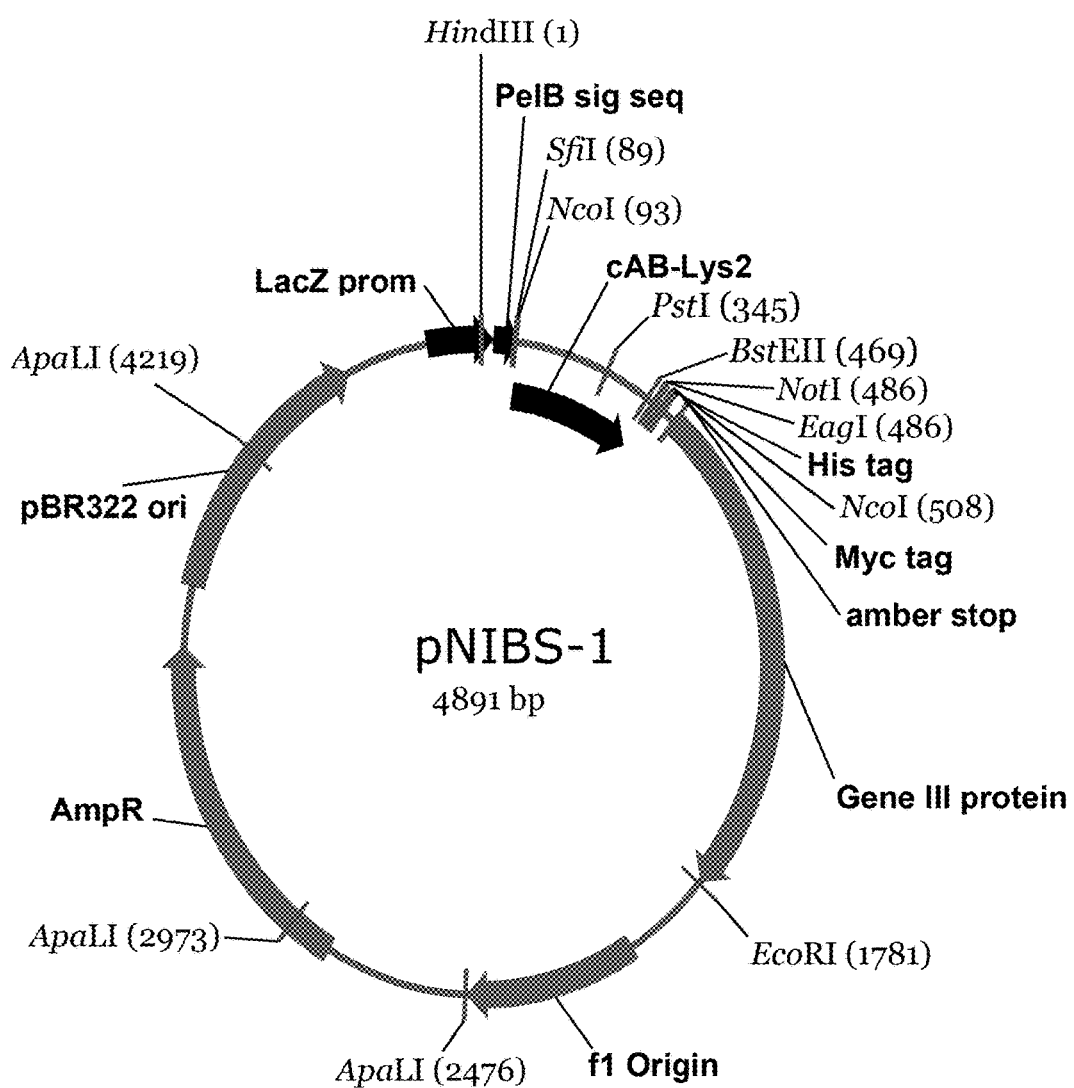

Klein et al.; "Epitope interactions of monoclonal anitobodies targeting CD20 and their relationship to functional properties"; mAbs; vol. 5 Issue 1; Jan. 2013; p. 22-33.
Yan et al.; "Construction of phage display VHH antibody library against avian H5N1 virus from alpaca"; Chinese Journal Immunology; vol. 27 No. 1; Jan. 2011; p. 44-49 (contains abstract).
Thanongsaksrikul et al.; "Botulinum Neurotoxins and Boutulism: A Novel Therapeutic Approach"; Toxins; vol. 3 No. 5; May 2011; p. 469-488.
Vincke et al.; "General Strategy to Humanize a Camelid Single-domain Antibody and Identification of a Universal Humanized Nanobody Scaffold"; J. Biol. Chem.; vol. 284 No. 5; Jan. 2009; p. 3273-3284.
Thanongsaksrikul et al.; "A VHH That Neutralizes the Zinc Metalloproteinase Activity of Botulinum Neurotoxin Type A"; J. Biol. Chem.; vol. 285 No. 13; Mar. 2010; p. 9657-9666.
Sui et al.; "Structural and functional bases for broad-spectrum neutralization of avian and human influenza A viruses"; Nature Structural and Molecular Biology; vol. 16 No. 3; Mar. 2009; p. 265-273.
Hufton et al.; "The Breadth of Cross Sub-Type Neutralisation Activity of a Single Domain Antibody to Influenza Hemagglutinin Can Be Increased by Antibody Valency"; PLOS one; vol. 9 No. 8; Aug. 2014; 19 pages.
European Patent Application No. 12756552.1; Rule 164(2)(b) and Article 94(3); dated Dec. 1, 2015; 13 pages.
European Patent Application No. 12756552.1; Rule 164(2)(a); dated Jul. 23, 2015; 7 pages.

\* cited by examiner

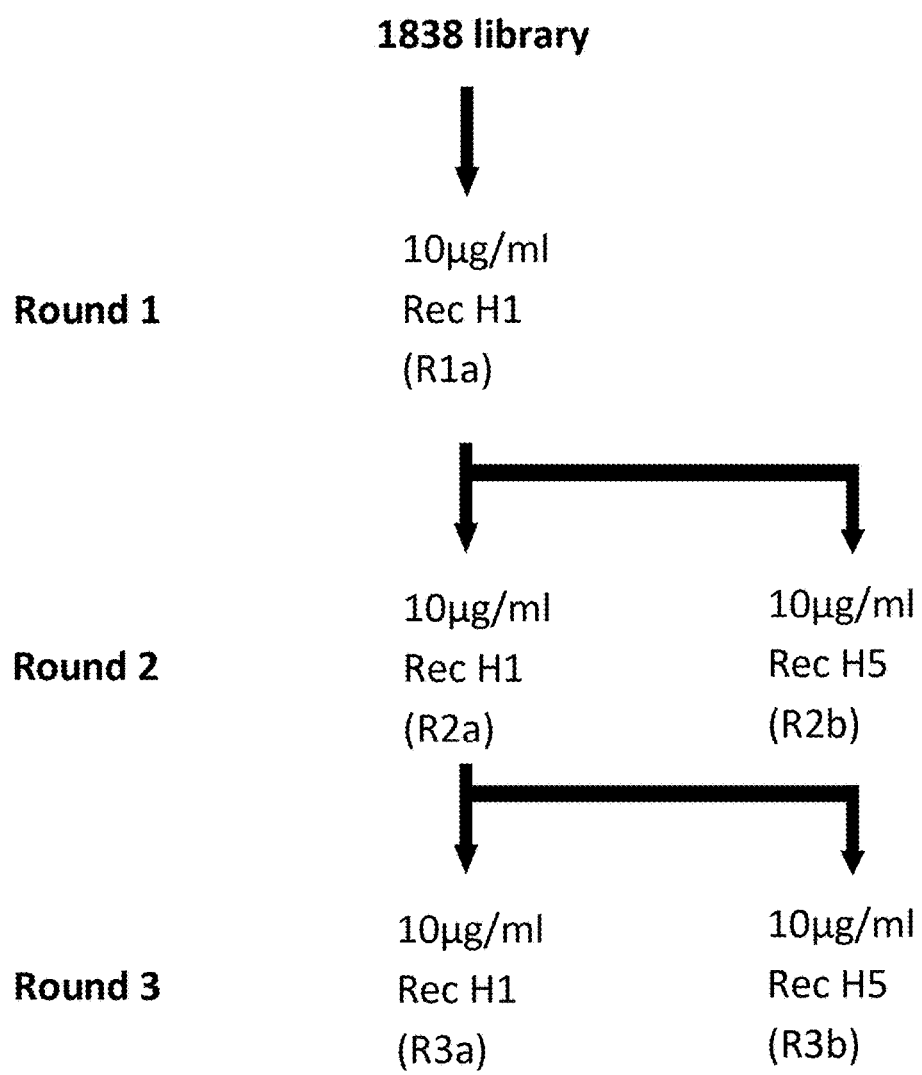

SEQUENCE LISTING

```
<160> NUMBER OF SEQ ID NOS: 133

<210> SEQ ID NO 1
<211> LENGTH: 9
<212> TYPE: PRT
<213> ORGANISM: Artificial Sequence
<220> FEATURE:
<223> OTHER INFORMATION: CDR3

<400> SEQUENCE: 1

Ser Thr Thr Thr Pro Pro Tyr Glu Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: CDR3

<400> SEQUENCE: 2

Arg Arg Asp Trp Arg Asp Tyr
1               5

<210> SEQ ID NO 3
<211> LENGTH: 7
<212> TYPE: PRT
<213> ORGANISM: Artificial Sequence
<220> FEATURE:
<223> OTHER INFORMATION: CDR3

<400> SEQUENCE: 3

Asn Pro Pro Gly Asn Leu Tyr
1               5
```

-continued

```
<210> SEQ ID NO 4
<211> LENGTH: 12
<212> TYPE: PRT
<213> ORGANISM: Artificial Sequence
<220> FEATURE:
<223> OTHER INFORMATION: CDR3

<400> SEQUENCE: 4

Asp Pro Leu Ser Thr Gly Trp Gly Gln Tyr Ser Tyr
1               5                   10

<210> SEQ ID NO 5
<211> LENGTH: 9
<212> TYPE: PRT
<213> ORGANISM: Artificial Sequence
<220> FEATURE:
<223> OTHER INFORMATION: CDR3

<400> SEQUENCE: 5

Ser Thr Thr Thr Pro Pro His Glu Phe
1               5

<210> SEQ ID NO 6
<211> LENGTH: 10
<212> TYPE: PRT
<213> ORGANISM: Artificial Sequence
<220> FEATURE:
<223> OTHER INFORMATION: CDR3

<400> SEQUENCE: 6

Arg Asp Gly Phe Phe Asn Arg Tyr Asp Tyr
1               5                   10

<210> SEQ ID NO 7
<211> LENGTH: 8
<212> TYPE: PRT
<213> ORGANISM: Artificial Sequence
<220> FEATURE:
<223> OTHER INFORMATION: CDR3

<400> SEQUENCE: 7

Ser Gly Pro Gly Gly Leu Asn Val
1               5

<210> SEQ ID NO 8
<211> LENGTH: 14
<212> TYPE: PRT
<213> ORGANISM: Artificial Sequence
<220> FEATURE:
<223> OTHER INFORMATION: CDR3

<400> SEQUENCE: 8

Thr Arg Trp Val Pro Thr Met Lys Ala Asp Glu Tyr Asn Tyr
1               5                   10

<210> SEQ ID NO 9
<211> LENGTH: 15
<212> TYPE: PRT
<213> ORGANISM: Artificial Sequence
<220> FEATURE:
<223> OTHER INFORMATION: CDR3

<400> SEQUENCE: 9

Ala Ser Trp Val Ala Ser Leu Trp Ser Pro Ser Glu Tyr Asp Tyr
1               5                   10                  15
```

```
<210> SEQ ID NO 10
<211> LENGTH: 7
<212> TYPE: PRT
<213> ORGANISM: Artificial Sequence
<220> FEATURE:
<223> OTHER INFORMATION: CDR3

<400> SEQUENCE: 10

Asp Pro Pro Gly Ile Leu Tyr
1               5

<210> SEQ ID NO 11
<211> LENGTH: 16
<212> TYPE: PRT
<213> ORGANISM: Artificial Sequence
<220> FEATURE:
<223> OTHER INFORMATION: CDR3

<400> SEQUENCE: 11

Asp Pro Val Cys Thr Ala Gly Trp Tyr Arg Pro Ser Arg Phe Asp Leu
1               5                   10                  15

<210> SEQ ID NO 12
<211> LENGTH: 9
<212> TYPE: PRT
<213> ORGANISM: Artificial Sequence
<220> FEATURE:
<223> OTHER INFORMATION: CDR3

<400> SEQUENCE: 12

Ser Thr Leu Thr Pro Pro His Glu Tyr
1               5

<210> SEQ ID NO 13
<211> LENGTH: 14
<212> TYPE: PRT
<213> ORGANISM: Artificial Sequence
<220> FEATURE:
<223> OTHER INFORMATION: CDR3

<400> SEQUENCE: 13

Gly Asn Thr Gly Ser Ser Asp Arg Ser Ser Tyr Val His
1               5                   10

<210> SEQ ID NO 14
<211> LENGTH: 9
<212> TYPE: PRT
<213> ORGANISM: Artificial Sequence
<220> FEATURE:
<223> OTHER INFORMATION: CDR3

<400> SEQUENCE: 14

Lys Ser Pro Leu Val Asp Asn Glu Tyr
1               5

<210> SEQ ID NO 15
<211> LENGTH: 19
<212> TYPE: PRT
<213> ORGANISM: Artificial Sequence
<220> FEATURE:
<223> OTHER INFORMATION: CDR3

<400> SEQUENCE: 15

Lys Gly Phe Ala Pro Phe Leu Ile Gly Cys Pro Trp Gly Lys Ala Glu
1               5                   10                  15

Tyr Asp Tyr
```

```
<210> SEQ ID NO 16
<211> LENGTH: 15
<212> TYPE: PRT
<213> ORGANISM: Artificial Sequence
<220> FEATURE:
<223> OTHER INFORMATION: CDR3

<400> SEQUENCE: 16

Thr Lys Ala Phe Gly Ile Ala Thr Ile Thr Ala Asp Tyr Glu Leu
1               5                   10                  15

<210> SEQ ID NO 17
<211> LENGTH: 9
<212> TYPE: PRT
<213> ORGANISM: Artificial Sequence
<220> FEATURE:
<223> OTHER INFORMATION: CDR3

<400> SEQUENCE: 17

Ser Ser Thr Val Ala Pro His Glu Tyr
1               5

<210> SEQ ID NO 18
<211> LENGTH: 8
<212> TYPE: PRT
<213> ORGANISM: Artificial Sequence
<220> FEATURE:
<223> OTHER INFORMATION: CDR3

<400> SEQUENCE: 18

Ser Gly Pro Gly Gly Val Glu Val
1               5

<210> SEQ ID NO 19
<211> LENGTH: 8
<212> TYPE: PRT
<213> ORGANISM: Artificial Sequence
<220> FEATURE:
<223> OTHER INFORMATION: CDR3

<400> SEQUENCE: 19

Ser Gly Pro Gly Gly Val Ile Leu
1               5

<210> SEQ ID NO 20
<211> LENGTH: 11
<212> TYPE: PRT
<213> ORGANISM: Artificial Sequence
<220> FEATURE:
<223> OTHER INFORMATION: CDR3

<400> SEQUENCE: 20

Lys Thr Ser Thr Thr Thr Pro Pro Tyr Glu Tyr
1               5                   10

<210> SEQ ID NO 21
<211> LENGTH: 9
<212> TYPE: PRT
<213> ORGANISM: Artificial Sequence
<220> FEATURE:
<223> OTHER INFORMATION: CDR3

<400> SEQUENCE: 21

Asn Thr Arg Arg Asp Trp Arg Asp Tyr
1               5
```

```
<210> SEQ ID NO 22
<211> LENGTH: 9
<212> TYPE: PRT
<213> ORGANISM: Artificial Sequence
<220> FEATURE:
<223> OTHER INFORMATION: CDR3

<400> SEQUENCE: 22

Asn Leu Asn Pro Pro Gly Asn Leu Tyr
1               5

<210> SEQ ID NO 23
<211> LENGTH: 14
<212> TYPE: PRT
<213> ORGANISM: Artificial Sequence
<220> FEATURE:
<223> OTHER INFORMATION: CDR3

<400> SEQUENCE: 23

Asn Ala Asp Pro Leu Ser Thr Gly Trp Gly Gln Tyr Ser Tyr
1               5                   10

<210> SEQ ID NO 24
<211> LENGTH: 11
<212> TYPE: PRT
<213> ORGANISM: Artificial Sequence
<220> FEATURE:
<223> OTHER INFORMATION: CDR3

<400> SEQUENCE: 24

Lys Cys Ser Thr Thr Thr Pro Pro His Glu Phe
1               5                   10

<210> SEQ ID NO 25
<211> LENGTH: 12
<212> TYPE: PRT
<213> ORGANISM: Artificial Sequence
<220> FEATURE:
<223> OTHER INFORMATION: CDR3

<400> SEQUENCE: 25

Asn Ala Arg Asp Gly Phe Phe Asn Arg Tyr Asp Tyr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: CDR3

<400> SEQUENCE: 26

Met Ala Ser Gly Pro Gly Gly Leu Asn Val
1               5                   10

<210> SEQ ID NO 27
<211> LENGTH: 16
<212> TYPE: PRT
<213> ORGANISM: Artificial Sequence
<220> FEATURE:
<223> OTHER INFORMATION: CDR3

<400> SEQUENCE: 27

Ala Gly Thr Arg Trp Val Pro Thr Met Lys Ala Asp Glu Tyr Asn Tyr
1               5                   10                  15
```

```
<210> SEQ ID NO 28
<211> LENGTH: 17
<212> TYPE: PRT
<213> ORGANISM: Artificial Sequence
<220> FEATURE:
<223> OTHER INFORMATION: CDR3

<400> SEQUENCE: 28

Ala Ala Ala Ser Trp Val Ala Ser Leu Trp Ser Pro Ser Glu Tyr Asp
1               5                   10                  15

Tyr

<210> SEQ ID NO 29
<211> LENGTH: 9
<212> TYPE: PRT
<213> ORGANISM: Artificial Sequence
<220> FEATURE:
<223> OTHER INFORMATION: CDR3

<400> SEQUENCE: 29

Asn Leu Asp Pro Pro Gly Ile Leu Tyr
1               5

<210> SEQ ID NO 30
<211> LENGTH: 18
<212> TYPE: PRT
<213> ORGANISM: Artificial Sequence
<220> FEATURE:
<223> OTHER INFORMATION: CDR3

<400> SEQUENCE: 30

Ala Ala Asp Pro Val Cys Thr Ala Gly Trp Tyr Arg Pro Ser Arg Phe
1               5                   10                  15

Asp Leu

<210> SEQ ID NO 31
<211> LENGTH: 11
<212> TYPE: PRT
<213> ORGANISM: Artificial Sequence
<220> FEATURE:
<223> OTHER INFORMATION: CDR3

<400> SEQUENCE: 31

Lys Ile Ser Thr Leu Thr Pro Pro His Glu Tyr
1               5                   10

<210> SEQ ID NO 32
<211> LENGTH: 16
<212> TYPE: PRT
<213> ORGANISM: Artificial Sequence
<220> FEATURE:
<223> OTHER INFORMATION: CDR3

<400> SEQUENCE: 32

Gly Ala Gly Asn Thr Gly Ser Ser Asp Arg Ser Ser Ser Tyr Val His
1               5                   10                  15

<210> SEQ ID NO 33
<211> LENGTH: 11
<212> TYPE: PRT
<213> ORGANISM: Artificial Sequence
<220> FEATURE:
<223> OTHER INFORMATION: CDR3
```

<400> SEQUENCE: 33

His Ala Lys Ser Pro Leu Val Asp Asn Glu Tyr
1               5                   10

<210> SEQ ID NO 34
<211> LENGTH: 21
<212> TYPE: PRT
<213> ORGANISM: Artificial Sequence
<220> FEATURE:
<223> OTHER INFORMATION: CDR3

<400> SEQUENCE: 34

Ala Val Lys Gly Phe Ala Pro Phe Leu Ile Gly Cys Pro Trp Gly Lys
1               5                   10                  15

Ala Glu Tyr Asp Tyr
            20

<210> SEQ ID NO 35
<211> LENGTH: 17
<212> TYPE: PRT
<213> ORGANISM: Artificial Sequence
<220> FEATURE:
<223> OTHER INFORMATION: CDR3

<400> SEQUENCE: 35

Ala Ala Thr Lys Ala Phe Gly Ile Ala Thr Ile Thr Ala Asp Tyr Glu
1               5                   10                  15

Leu

<210> SEQ ID NO 36
<211> LENGTH: 11
<212> TYPE: PRT
<213> ORGANISM: Artificial Sequence
<220> FEATURE:
<223> OTHER INFORMATION: CDR3

<400> SEQUENCE: 36

Lys Phe Ser Ser Thr Val Ala Pro His Glu Tyr
1               5                   10

<210> SEQ ID NO 37
<211> LENGTH: 10
<212> TYPE: PRT
<213> ORGANISM: Artificial Sequence
<220> FEATURE:
<223> OTHER INFORMATION: CDR3

<400> SEQUENCE: 37

Lys Ala Ser Gly Pro Gly Gly Val Glu Val
1               5                   10

<210> SEQ ID NO 38
<211> LENGTH: 10
<212> TYPE: PRT
<213> ORGANISM: Artificial Sequence
<220> FEATURE:
<223> OTHER INFORMATION: CDR3

<400> SEQUENCE: 38

Lys Ala Ser Gly Pro Gly Gly Val Ile Leu
1               5                   10

```
<210> SEQ ID NO 39
<211> LENGTH: 16
<212> TYPE: PRT
<213> ORGANISM: Artificial Sequence
<220> FEATURE:
<223> OTHER INFORMATION: CDR2

<400> SEQUENCE: 39

Val Ile Gly Asn Tyr Gly Asn Thr Asn Tyr Ala Asp Ser Val Lys Arg
1               5                   10                  15

<210> SEQ ID NO 40
<211> LENGTH: 17
<212> TYPE: PRT
<213> ORGANISM: Artificial Sequence
<220> FEATURE:
<223> OTHER INFORMATION: CDR2

<400> SEQUENCE: 40

Asp Ile Ala Ser Thr Arg Gly Thr Thr Asn Tyr Ala Asp Ser Val Lys
1               5                   10                  15

Gly

<210> SEQ ID NO 41
<211> LENGTH: 16
<212> TYPE: PRT
<213> ORGANISM: Artificial Sequence
<220> FEATURE:
<223> OTHER INFORMATION: CDR2

<400> SEQUENCE: 41

Gly Ile Thr Tyr Asp Asp Ser Thr Asn Tyr Ala Gly Ser Val Lys Gly
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: CDR2

<400> SEQUENCE: 42

Ala Ile Thr Ser Gly Glu Ser Thr Asn Tyr Ala Asp Ser Val Lys Gly
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: CDR2

<400> SEQUENCE: 43

Val Ile Gly Asn Tyr Gly Asn Thr Asn Tyr Ala Asp Ser Val Lys Gly
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: CDR2

<400> SEQUENCE: 44

Ala Val Thr Thr Asp Gly Ser Thr Ser Tyr Ala Asp Tyr Ala Lys Gly
1               5                   10                  15
```

```
<210> SEQ ID NO 45
<211> LENGTH: 16
<212> TYPE: PRT
<213> ORGANISM: Artificial Sequence
<220> FEATURE:
<223> OTHER INFORMATION: CDR2

<400> SEQUENCE: 45

Val Ile Gly Asn Gly Gly Asn Thr Asn Tyr Ala Glu Ser Val Lys Gly
1               5                   10                  15

<210> SEQ ID NO 46
<211> LENGTH: 17
<212> TYPE: PRT
<213> ORGANISM: Artificial Sequence
<220> FEATURE:
<223> OTHER INFORMATION: CDR2

<400> SEQUENCE: 46

Phe Ile Thr Ser Thr Ser Ala Val Thr Lys Tyr Ala Asp Ser Val Lys
1               5                   10                  15

Gly

<210> SEQ ID NO 47
<211> LENGTH: 16
<212> TYPE: PRT
<213> ORGANISM: Artificial Sequence
<220> FEATURE:
<223> OTHER INFORMATION: CDR2

<400> SEQUENCE: 47

Cys Arg Ala Ser Asp Gly Asn Thr Tyr Tyr Ala Glu Ser Leu Lys Gly
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: CDR2

<400> SEQUENCE: 48

Ser Ile Ala Tyr Asp Gly Ser Thr Ser Tyr Ala Asp Pro Val Lys Gly
1               5                   10                  15

<210> SEQ ID NO 49
<211> LENGTH: 17
<212> TYPE: PRT
<213> ORGANISM: Artificial Sequence
<220> FEATURE:
<223> OTHER INFORMATION: CDR2

<400> SEQUENCE: 49

Cys Ile Ser Pro Ser Asp Ser Phe Thr Glu Tyr Gly Asp Ser Val Lys
1               5                   10                  15

Gly

<210> SEQ ID NO 50
<211> LENGTH: 16
<212> TYPE: PRT
<213> ORGANISM: Artificial Sequence
<220> FEATURE:
<223> OTHER INFORMATION: CDR2
```

```
<400> SEQUENCE: 50

Val Ile Gly Asn Asn Asp Asn Thr Val Tyr Gly Asp Ser Val Gln Gly
1               5                   10                  15

<210> SEQ ID NO 51
<211> LENGTH: 17
<212> TYPE: PRT
<213> ORGANISM: Artificial Sequence
<220> FEATURE:
<223> OTHER INFORMATION: CDR2

<400> SEQUENCE: 51

Ala Ile Asp Trp Gly Asp Gly Pro Thr Thr Tyr Ala Asp Ser Val Lys
1               5                   10                  15

Gly

<210> SEQ ID NO 52
<211> LENGTH: 16
<212> TYPE: PRT
<213> ORGANISM: Artificial Sequence
<220> FEATURE:
<223> OTHER INFORMATION: CDR2

<400> SEQUENCE: 52

Ser Ile Asp Gly Arg Gly Thr Pro Met Tyr Ala Asp Ser Val Lys Gly
1               5                   10                  15

<210> SEQ ID NO 53
<211> LENGTH: 17
<212> TYPE: PRT
<213> ORGANISM: Artificial Sequence
<220> FEATURE:
<223> OTHER INFORMATION: CDR2

<400> SEQUENCE: 53

Cys Met Asn Ser Arg Asp Gly Thr Thr Asn Tyr Ala Asp Ser Val Lys
1               5                   10                  15

Gly

<210> SEQ ID NO 54
<211> LENGTH: 16
<212> TYPE: PRT
<213> ORGANISM: Artificial Sequence
<220> FEATURE:
<223> OTHER INFORMATION: CDR2

<400> SEQUENCE: 54

Ala Ile Thr Ala Gly Gly Asn Thr Tyr Tyr Ala Asp Ser Ala Lys Ala
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: CDR2

<400> SEQUENCE: 55

Val Ile Gly Asn Tyr Gly Asn Thr Asn Tyr Ala Asp Ser Val Lys Gly
1               5                   10                  15

<210> SEQ ID NO 56
<211> LENGTH: 16
<212> TYPE: PRT
<213> ORGANISM: Artificial Sequence
```

```
<220> FEATURE:
<223> OTHER INFORMATION: CDR2

<400> SEQUENCE: 56

Val Ile Gly Asn Gly Gly Asn Thr Asn Tyr Ala Asp Ser Val Lys Gly
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: CDR2

<400> SEQUENCE: 57

Val Ile Gly Asn Gly Gly Thr Asn Tyr Ala Asp Ser Val Lys Gly
1               5                   10                  15

<210> SEQ ID NO 58
<211> LENGTH: 7
<212> TYPE: PRT
<213> ORGANISM: Artificial Sequence
<220> FEATURE:
<223> OTHER INFORMATION: CDR2

<400> SEQUENCE: 58

Ile Gly Asn Tyr Gly Asn Thr
1               5

<210> SEQ ID NO 59
<211> LENGTH: 8
<212> TYPE: PRT
<213> ORGANISM: Artificial Sequence
<220> FEATURE:
<223> OTHER INFORMATION: CDR2

<400> SEQUENCE: 59

Ile Ala Ser Thr Arg Gly Thr Thr
1               5

<210> SEQ ID NO 60
<211> LENGTH: 7
<212> TYPE: PRT
<213> ORGANISM: Artificial Sequence
<220> FEATURE:
<223> OTHER INFORMATION: CDR2

<400> SEQUENCE: 60

Ile Thr Tyr Asp Asp Ser Thr
1               5

<210> SEQ ID NO 61
<211> LENGTH: 7
<212> TYPE: PRT
<213> ORGANISM: Artificial Sequence
<220> FEATURE:
<223> OTHER INFORMATION: CDR2

<400> SEQUENCE: 61

Ile Thr Ser Gly Glu Ser Thr
1               5

<210> SEQ ID NO 62
<211> LENGTH: 7
<212> TYPE: PRT
<213> ORGANISM: Artificial Sequence
```

```
<220> FEATURE:
<223> OTHER INFORMATION: CDR2

<400> SEQUENCE: 62

Ile Gly Asn Tyr Gly Asn Thr
1               5

<210> SEQ ID NO 63
<211> LENGTH: 7
<212> TYPE: PRT
<213> ORGANISM: Artificial Sequence
<220> FEATURE:
<223> OTHER INFORMATION: CDR2

<400> SEQUENCE: 63

Val Thr Thr Asp Gly Ser Thr
1               5

<210> SEQ ID NO 64
<211> LENGTH: 7
<212> TYPE: PRT
<213> ORGANISM: Artificial Sequence
<220> FEATURE:
<223> OTHER INFORMATION: CDR2

<400> SEQUENCE: 64

Ile Gly Asn Gly Gly Asn Thr
1               5

<210> SEQ ID NO 65
<211> LENGTH: 8
<212> TYPE: PRT
<213> ORGANISM: Artificial Sequence
<220> FEATURE:
<223> OTHER INFORMATION: CDR2

<400> SEQUENCE: 65

Ile Thr Ser Thr Ser Ala Val Thr
1               5

<210> SEQ ID NO 66
<211> LENGTH: 7
<212> TYPE: PRT
<213> ORGANISM: Artificial Sequence
<220> FEATURE:
<223> OTHER INFORMATION: CDR2

<400> SEQUENCE: 66

Arg Ala Ser Asp Gly Asn Thr
1               5

<210> SEQ ID NO 67
<211> LENGTH: 7
<212> TYPE: PRT
<213> ORGANISM: Artificial Sequence
<220> FEATURE:
<223> OTHER INFORMATION: CDR2

<400> SEQUENCE: 67

Ile Ala Tyr Asp Gly Ser Thr
1               5

<210> SEQ ID NO 68
<211> LENGTH: 8
<212> TYPE: PRT
<213> ORGANISM: Artificial Sequence
```

```
<220> FEATURE:
<223> OTHER INFORMATION: CDR2

<400> SEQUENCE: 68

Ile Ser Pro Ser Asp Ser Phe Thr
1               5

<210> SEQ ID NO 69
<211> LENGTH: 7
<212> TYPE: PRT
<213> ORGANISM: Artificial Sequence
<220> FEATURE:
<223> OTHER INFORMATION: CDR2

<400> SEQUENCE: 69

Ile Gly Asn Asn Asp Asn Thr
1               5

<210> SEQ ID NO 70
<211> LENGTH: 8
<212> TYPE: PRT
<213> ORGANISM: Artificial Sequence
<220> FEATURE:
<223> OTHER INFORMATION: CDR2

<400> SEQUENCE: 70

Ile Asp Trp Gly Asp Gly Pro Thr
1               5

<210> SEQ ID NO 71
<211> LENGTH: 7
<212> TYPE: PRT
<213> ORGANISM: Artificial Sequence
<220> FEATURE:
<223> OTHER INFORMATION: CDR2

<400> SEQUENCE: 71

Ile Asp Gly Arg Gly Thr Pro
1               5

<210> SEQ ID NO 72
<211> LENGTH: 8
<212> TYPE: PRT
<213> ORGANISM: Artificial Sequence
<220> FEATURE:
<223> OTHER INFORMATION: CDR2

<400> SEQUENCE: 72

Met Asn Ser Arg Asp Gly Thr Thr
1               5

<210> SEQ ID NO 73
<211> LENGTH: 7
<212> TYPE: PRT
<213> ORGANISM: Artificial Sequence
<220> FEATURE:
<223> OTHER INFORMATION: CDR2

<400> SEQUENCE: 73

Ile Thr Ala Gly Gly Asn Thr
1               5

<210> SEQ ID NO 74
<211> LENGTH: 7
<212> TYPE: PRT
<213> ORGANISM: Artificial Sequence
```

```
<220> FEATURE:
<223> OTHER INFORMATION: CDR2

<400> SEQUENCE: 74

Ile Gly Asn Tyr Gly Asn Thr
1               5

<210> SEQ ID NO 75
<211> LENGTH: 7
<212> TYPE: PRT
<213> ORGANISM: Artificial Sequence
<220> FEATURE:
<223> OTHER INFORMATION: CDR2

<400> SEQUENCE: 75

Ile Gly Asn Gly Gly Asn Thr
1               5

<210> SEQ ID NO 76
<211> LENGTH: 7
<212> TYPE: PRT
<213> ORGANISM: Artificial Sequence
<220> FEATURE:
<223> OTHER INFORMATION: CDR2

<400> SEQUENCE: 76

Ile Gly Asn Gly Gly Asn Thr
1               5

<210> SEQ ID NO 77
<211> LENGTH: 5
<212> TYPE: PRT
<213> ORGANISM: Artificial Sequence
<220> FEATURE:
<223> OTHER INFORMATION: CDR1

<400> SEQUENCE: 77

Ile Val Thr Met Gly
1               5

<210> SEQ ID NO 78
<211> LENGTH: 5
<212> TYPE: PRT
<213> ORGANISM: Artificial Sequence
<220> FEATURE:
<223> OTHER INFORMATION: CDR1

<400> SEQUENCE: 78

Trp Tyr Asp Val Gly
1               5

<210> SEQ ID NO 79
<211> LENGTH: 5
<212> TYPE: PRT
<213> ORGANISM: Artificial Sequence
<220> FEATURE:
<223> OTHER INFORMATION: CDR1

<400> SEQUENCE: 79

Arg Tyr Arg Met Gly
1               5

<210> SEQ ID NO 80
<211> LENGTH: 5
<212> TYPE: PRT
<213> ORGANISM: Artificial Sequence
```

```
<220> FEATURE:
<223> OTHER INFORMATION: CDR1

<400> SEQUENCE: 80

Leu Tyr Thr Met Gly
1               5

<210> SEQ ID NO 81
<211> LENGTH: 5
<212> TYPE: PRT
<213> ORGANISM: Artificial Sequence
<220> FEATURE:
<223> OTHER INFORMATION: CDR1

<400> SEQUENCE: 81

Ile Val Thr Met Gly
1               5

<210> SEQ ID NO 82
<211> LENGTH: 5
<212> TYPE: PRT
<213> ORGANISM: Artificial Sequence
<220> FEATURE:
<223> OTHER INFORMATION: CDR1

<400> SEQUENCE: 82

Thr Tyr Pro Met Ser
1               5

<210> SEQ ID NO 83
<211> LENGTH: 5
<212> TYPE: PRT
<213> ORGANISM: Artificial Sequence
<220> FEATURE:
<223> OTHER INFORMATION: CDR1

<400> SEQUENCE: 83

Phe Tyr Thr Met Gly
1               5

<210> SEQ ID NO 84
<211> LENGTH: 5
<212> TYPE: PRT
<213> ORGANISM: Artificial Sequence
<220> FEATURE:
<223> OTHER INFORMATION: CDR1

<400> SEQUENCE: 84

Asn Tyr Ala Ile Gly
1               5

<210> SEQ ID NO 85
<211> LENGTH: 5
<212> TYPE: PRT
<213> ORGANISM: Artificial Sequence
<220> FEATURE:
<223> OTHER INFORMATION: CDR1

<400> SEQUENCE: 85

Gly Tyr Ala Ile Ala
1               5

<210> SEQ ID NO 86
<211> LENGTH: 5
<212> TYPE: PRT
<213> ORGANISM: Artificial Sequence
```

```
<220> FEATURE:
<223> OTHER INFORMATION: CDR1

<400> SEQUENCE: 86

Arg Tyr Arg Met Gly
1               5

<210> SEQ ID NO 87
<211> LENGTH: 5
<212> TYPE: PRT
<213> ORGANISM: Artificial Sequence
<220> FEATURE:
<223> OTHER INFORMATION: CDR1

<400> SEQUENCE: 87

Ala Tyr Ala Ile Ala
1               5

<210> SEQ ID NO 88
<211> LENGTH: 5
<212> TYPE: PRT
<213> ORGANISM: Artificial Sequence
<220> FEATURE:
<223> OTHER INFORMATION: CDR1

<400> SEQUENCE: 88

Ile Ile Thr Met Gly
1               5

<210> SEQ ID NO 89
<211> LENGTH: 5
<212> TYPE: PRT
<213> ORGANISM: Artificial Sequence
<220> FEATURE:
<223> OTHER INFORMATION: CDR1

<400> SEQUENCE: 89

Leu Tyr Arg Val Gly
1               5

<210> SEQ ID NO 90
<211> LENGTH: 5
<212> TYPE: PRT
<213> ORGANISM: Artificial Sequence
<220> FEATURE:
<223> OTHER INFORMATION: CDR1

<400> SEQUENCE: 90

Met Tyr Met Ile Asp
1               5

<210> SEQ ID NO 91
<211> LENGTH: 5
<212> TYPE: PRT
<213> ORGANISM: Artificial Sequence
<220> FEATURE:
<223> OTHER INFORMATION: CDR1

<400> SEQUENCE: 91

Asn Asn Ala Ile Gly
1               5

<210> SEQ ID NO 92
<211> LENGTH: 5
<212> TYPE: PRT
<213> ORGANISM: Artificial Sequence
```

```
<220> FEATURE:
<223> OTHER INFORMATION: CDR1

<400> SEQUENCE: 92

Ile Asn Ala Met Gly
1               5

<210> SEQ ID NO 93
<211> LENGTH: 5
<212> TYPE: PRT
<213> ORGANISM: Artificial Sequence
<220> FEATURE:
<223> OTHER INFORMATION: CDR1

<400> SEQUENCE: 93

Ile Val Thr Met Gly
1               5

<210> SEQ ID NO 94
<211> LENGTH: 5
<212> TYPE: PRT
<213> ORGANISM: Artificial Sequence
<220> FEATURE:
<223> OTHER INFORMATION: CDR1

<400> SEQUENCE: 94

Phe Tyr Thr Met Gly
1               5

<210> SEQ ID NO 95
<211> LENGTH: 5
<212> TYPE: PRT
<213> ORGANISM: Artificial Sequence
<220> FEATURE:
<223> OTHER INFORMATION: CDR1

<400> SEQUENCE: 95

Phe Tyr Thr Met Gly
1               5

<210> SEQ ID NO 96
<211> LENGTH: 8
<212> TYPE: PRT
<213> ORGANISM: Artificial Sequence
<220> FEATURE:
<223> OTHER INFORMATION: CDR1

<400> SEQUENCE: 96

Gly Ser Ile Ser Arg Ile Val Thr
1               5

<210> SEQ ID NO 97
<211> LENGTH: 8
<212> TYPE: PRT
<213> ORGANISM: Artificial Sequence
<220> FEATURE:
<223> OTHER INFORMATION: CDR1

<400> SEQUENCE: 97

Gly Phe Thr Phe Ser Trp Tyr Asp
1               5

<210> SEQ ID NO 98
<211> LENGTH: 8
<212> TYPE: PRT
<213> ORGANISM: Artificial Sequence
```

```
<220> FEATURE:
<223> OTHER INFORMATION: CDR1

<400> SEQUENCE: 98

Gly Ser Phe Phe Ser Arg Tyr Arg
1               5

<210> SEQ ID NO 99
<211> LENGTH: 8
<212> TYPE: PRT
<213> ORGANISM: Artificial Sequence
<220> FEATURE:
<223> OTHER INFORMATION: CDR1

<400> SEQUENCE: 99

Gly Ser Ala Phe Ser Leu Tyr Thr
1               5

<210> SEQ ID NO 100
<211> LENGTH: 8
<212> TYPE: PRT
<213> ORGANISM: Artificial Sequence
<220> FEATURE:
<223> OTHER INFORMATION: CDR1

<400> SEQUENCE: 100

Gly Ser Ile Ser Arg Ile Val Thr
1               5

<210> SEQ ID NO 101
<211> LENGTH: 10
<212> TYPE: PRT
<213> ORGANISM: Artificial Sequence
<220> FEATURE:
<223> OTHER INFORMATION: CDR1

<400> SEQUENCE: 101

Gly Ser Ala Val Leu Phe Ser Thr Tyr Pro
1               5                   10

<210> SEQ ID NO 102
<211> LENGTH: 8
<212> TYPE: PRT
<213> ORGANISM: Artificial Sequence
<220> FEATURE:
<223> OTHER INFORMATION: CDR1

<400> SEQUENCE: 102

Asn Asp Ile Phe Ser Phe Tyr Thr
1               5

<210> SEQ ID NO 103
<211> LENGTH: 8
<212> TYPE: PRT
<213> ORGANISM: Artificial Sequence
<220> FEATURE:
<223> OTHER INFORMATION: CDR1

<400> SEQUENCE: 103

Gly Phe Ser Leu Asp Asn Tyr Ala
1               5

<210> SEQ ID NO 104
<211> LENGTH: 8
<212> TYPE: PRT
<213> ORGANISM: Artificial Sequence
```

```
<220> FEATURE:
<223> OTHER INFORMATION: CDR1

<400> SEQUENCE: 104

Gly Phe Pro Phe Asp Gly Tyr Ala
1               5

<210> SEQ ID NO 105
<211> LENGTH: 8
<212> TYPE: PRT
<213> ORGANISM: Artificial Sequence
<220> FEATURE:
<223> OTHER INFORMATION: CDR1

<400> SEQUENCE: 105

Gly Ser Phe Phe Ser Arg Tyr Arg
1               5

<210> SEQ ID NO 106
<211> LENGTH: 8
<212> TYPE: PRT
<213> ORGANISM: Artificial Sequence
<220> FEATURE:
<223> OTHER INFORMATION: CDR1

<400> SEQUENCE: 106

Gly Phe Thr Leu Gly Ala Tyr Ala
1               5

<210> SEQ ID NO 107
<211> LENGTH: 8
<212> TYPE: PRT
<213> ORGANISM: Artificial Sequence
<220> FEATURE:
<223> OTHER INFORMATION: CDR1

<400> SEQUENCE: 107

Gly Ser Met Ser Arg Ile Ile Thr
1               5

<210> SEQ ID NO 108
<211> LENGTH: 8
<212> TYPE: PRT
<213> ORGANISM: Artificial Sequence
<220> FEATURE:
<223> OTHER INFORMATION: CDR1

<400> SEQUENCE: 108

Val Leu Thr Phe Ser Leu Tyr Arg
1               5

<210> SEQ ID NO 109
<211> LENGTH: 8
<212> TYPE: PRT
<213> ORGANISM: Artificial Sequence
<220> FEATURE:
<223> OTHER INFORMATION: CDR1

<400> SEQUENCE: 109

Gly Asp Ile Phe Val Met Tyr Met
1               5

<210> SEQ ID NO 110
<211> LENGTH: 8
<212> TYPE: PRT
<213> ORGANISM: Artificial Sequence
```

```
<220> FEATURE:
<223> OTHER INFORMATION: CDR1

<400> SEQUENCE: 110

Gly Ser Thr Leu Asn Asn Ala
1               5

<210> SEQ ID NO 111
<211> LENGTH: 8
<212> TYPE: PRT
<213> ORGANISM: Artificial Sequence
<220> FEATURE:
<223> OTHER INFORMATION: CDR1

<400> SEQUENCE: 111

Gly Ser Ala Phe Ser Ile Asn Ala
1               5

<210> SEQ ID NO 112
<211> LENGTH: 8
<212> TYPE: PRT
<213> ORGANISM: Artificial Sequence
<220> FEATURE:
<223> OTHER INFORMATION: CDR1

<400> SEQUENCE: 112

Gly Ser Ile Ser Ser Ile Val Thr
1               5

<210> SEQ ID NO 113
<211> LENGTH: 8
<212> TYPE: PRT
<213> ORGANISM: Artificial Sequence
<220> FEATURE:
<223> OTHER INFORMATION: CDR1

<400> SEQUENCE: 113

Asp Asn Ile Phe Ser Phe Tyr Thr
1               5

<210> SEQ ID NO 114
<211> LENGTH: 8
<212> TYPE: PRT
<213> ORGANISM: Artificial Sequence
<220> FEATURE:
<223> OTHER INFORMATION: CDR1

<400> SEQUENCE: 114

Thr Asn Ile Ala Ser Phe Tyr Thr
1               5

<210> SEQ ID NO 115
<211> LENGTH: 117
<212> TYPE: PRT
<213> ORGANISM: Artificial Sequence
<220> FEATURE:
<223> OTHER INFORMATION: Full length VHH

<400> SEQUENCE: 115

Gln Leu Gln Leu Val Glu Ser Gly Gly Gly Leu Val Gln Pro Gly Gly
1               5                   10                  15

Ser Leu Arg Leu Ser Cys Ala Ala Ser Gly Ser Ile Ser Arg Ile Val
            20                  25                  30

Thr Met Gly Trp Tyr Arg Gln Ala Ser Gly Lys Glu Arg Glu Leu Val
        35                  40                  45
```

```
Ala Val Ile Gly Asn Tyr Gly Asn Thr Asn Tyr Ala Asp Ser Val Lys
         50                  55                  60

Gly Arg Phe Thr Val Ser Arg Asp Asn Ala Lys Asp Thr Ala Tyr Leu
 65                  70                  75                  80

Gln Met Asn Gly Leu Asn Val Glu Asp Thr Ala Ile Tyr Tyr Cys Lys
                 85                  90                  95

Thr Ser Thr Thr Thr Pro Pro Tyr Glu Tyr Trp Gly Gln Gly Thr Gln
             100                 105                 110

Val Thr Val Ser Ser
            115

<210> SEQ ID NO 116
<211> LENGTH: 116
<212> TYPE: PRT
<213> ORGANISM: Artificial Sequence
<220> FEATURE:
<223> OTHER INFORMATION: Full length VHH

<400> SEQUENCE: 116

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
                 20                  25                  30

Asp Val Gly Trp Tyr Arg Arg Ala Pro Gly Lys Glu Arg Glu Leu Val
             35                  40                  45

Ala Asp Ile Ala Ser Thr Arg Gly Thr Thr Asn Tyr Ala Asp Ser Val
         50                  55                  60

Lys Gly Arg Phe Thr Ile Ser Arg Asp Asn Ala Lys Asn Ser Val Tyr
 65                  70                  75                  80

Leu Gln Met Asn Ser Leu Lys Pro Glu Asp Thr Ala Val Tyr Tyr Cys
                 85                  90                  95

Asn Thr Arg Arg Asp Trp Arg Asp Tyr Trp Gly Gln Gly Ile Gln Val
             100                 105                 110

Thr Val Ser Ser
            115

<210> SEQ ID NO 117
<211> LENGTH: 115
<212> TYPE: PRT
<213> ORGANISM: Artificial Sequence
<220> FEATURE:
<223> OTHER INFORMATION: Full length VHH

<400> SEQUENCE: 117

Gln Val Gln Leu Val Glu Ser Gly Gly Gly Leu Val Gln Pro Gly Gly
 1               5                  10                  15

Ser Leu Arg Leu Ser Cys Ala Ala Ser Gly Ser Phe Phe Ser Arg Tyr
                 20                  25                  30

Arg Met Gly Trp Tyr Arg Gln Ala Pro Gly Glu Gln Arg Glu Leu Val
             35                  40                  45

Ala Gly Ile Thr Tyr Asp Asp Ser Thr Asn Tyr Ala Gly Ser Val Lys
         50                  55                  60

Gly Arg Phe Thr Ile Ser Arg Asp Asn Ala Lys Asn Thr Val His Leu
 65                  70                  75                  80

Gln Met Asn Ser Leu Lys Pro Glu Asp Thr Ala Val Tyr Tyr Cys Asn
                 85                  90                  95
```

```
Leu Asn Pro Pro Gly Asn Leu Tyr Trp Gly Gln Gly Thr Gln Val Thr
            100                 105                 110

Val Ser Ser
        115

<210> SEQ ID NO 118
<211> LENGTH: 120
<212> TYPE: PRT
<213> ORGANISM: Artificial Sequence
<220> FEATURE:
<223> OTHER INFORMATION: Full length VHH

<400> SEQUENCE: 118

Gln Val Gln Leu Val Glu Ser Gly Gly Gly Leu Val Gln Pro Gly Gly
1               5                   10                  15

Ser Leu Arg Leu Ser Cys Leu Ala Ser Gly Ser Ala Phe Ser Leu Tyr
            20                  25                  30

Thr Met Gly Trp Tyr Arg Gln Ala Pro Gly Asn Gln Arg Glu Leu Val
        35                  40                  45

Ala Ala Ile Thr Ser Gly Glu Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Pro Leu Ser Thr Gly Trp Gly Gln Tyr Ser Tyr Trp Gly Gln
            100                 105                 110

Gly Thr Gln Val Thr Val Ser Ser
        115                 120

<210> SEQ ID NO 119
<211> LENGTH: 117
<212> TYPE: PRT
<213> ORGANISM: Artificial Sequence
<220> FEATURE:
<223> OTHER INFORMATION: Full length VHH

<400> SEQUENCE: 119

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ser Arg Ile Val
            20                  25                  30

Thr Met Gly Trp Tyr Arg Gln Gly Pro Gly Lys Glu Arg Glu Leu Val
        35                  40                  45

Ala Val Ile Gly Asn Tyr Gly Asn Thr Asn Tyr Ala Asp Ser Val Lys
    50                  55                  60

Gly Arg Phe Thr Val Ser Arg Asp Asn Ala Lys Asp Thr Ala Tyr Leu
65                  70                  75                  80

Gln Met Asn Asn Leu Asn Val Glu Asp Thr Ala Met Tyr Tyr Cys Lys
                85                  90                  95

Cys Ser Thr Thr Thr Pro Pro His Glu Phe Trp Gly Gln Gly Thr Gln
            100                 105                 110

Val Thr Val Ser Ser
        115

<210> SEQ ID NO 120
<211> LENGTH: 120
<212> TYPE: PRT
<213> ORGANISM: Artificial Sequence
```

<220> FEATURE:
<223> OTHER INFORMATION: Full length VHH

<400> SEQUENCE: 120

Gln Val Gln Leu Val Glu Ser Gly Gly Gly Leu Val Gln Pro Gly Gly
1               5                   10                  15

Ser Leu Arg Leu Ser Cys Ser Ala Ser Gly Ser Ala Val Leu Phe Ser
            20                  25                  30

Thr Tyr Pro Met Ser Trp Tyr Arg Gln Ala Pro Gly Lys Gln Arg Glu
        35                  40                  45

Leu Val Ala Ala Val Thr Thr Asp Gly Ser Thr Ser Tyr Ala Asp Tyr
    50                  55                  60

Ala Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Asn Ala Arg Asp Gly Phe Phe Asn Arg Tyr Asp Tyr Trp Gly Gln
            100                 105                 110

Gly Thr Gln Val Thr Val Ser Ser
        115                 120

<210> SEQ ID NO 121
<211> LENGTH: 116
<212> TYPE: PRT
<213> ORGANISM: Artificial Sequence
<220> FEATURE:
<223> OTHER INFORMATION: Full length VHH

<400> SEQUENCE: 121

Gln Val Gln Leu Val Glu Ser Gly Gly Gly Leu Val Gln Pro Gly Gly
1               5                   10                  15

Ser Leu Arg Leu Ser Cys Ala Ala Ser Asn Asp Ile Phe Ser Phe Tyr
            20                  25                  30

Thr Met Gly Trp Tyr Leu Gln Ala Ile Gly Lys Gln Arg Glu Pro Val
        35                  40                  45

Ala Val Ile Gly Asn Gly Gly Asn Thr Asn Tyr Ala Glu Ser Val Lys
    50                  55                  60

Gly Arg Phe Thr Ile Ser Arg Asp Gly Ala Lys Asn Thr Ala Tyr Leu
65                  70                  75                  80

Gln Met Asn Ser Leu Lys Pro Glu Asp Thr Ala Val Tyr Tyr Cys Met
                85                  90                  95

Ala Ser Gly Pro Gly Gly Leu Asn Val Trp Gly Gln Gly Thr Gln Val
            100                 105                 110

Thr Val Ser Ser
        115

<210> SEQ ID NO 122
<211> LENGTH: 123
<212> TYPE: PRT
<213> ORGANISM: Artificial Sequence
<220> FEATURE:
<223> OTHER INFORMATION: Full length VHH

<400> SEQUENCE: 122

Gln Leu Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Asp Asn Tyr
            20                  25                  30

```
Ala Ile Gly Trp Phe Arg Arg Ala Pro Gly Glu Glu Arg Glu Gly Val
        35                  40                  45

Ser Phe Ile Thr Ser Thr Ser Ala Val Thr Lys Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Thr Ser Leu Lys Pro Glu Asp Thr Ala Val Tyr Tyr Cys
                 85                  90                  95

Ala Gly Thr Arg Trp Val Pro Thr Met Lys Ala Asp Glu Tyr Asn Tyr
             100                 105                 110

Trp Gly Gln Gly Thr Gln Val Thr Val Ser Ser
             115                 120
```

<210> SEQ ID NO 123
<211> LENGTH: 123
<212> TYPE: PRT
<213> ORGANISM: Artificial Sequence
<220> FEATURE:
<223> OTHER INFORMATION: Full length VHH

<400> SEQUENCE: 123

```
Gln Leu Gln Leu Val Glu Ser Gly Gly Gly Leu Val Gln Val Gly Gly
 1               5                   10                  15

Ser Leu Arg Leu Ser Cys Ala Ala Ser Gly Phe Pro Phe Asp Gly Tyr
             20                  25                  30

Ala Ile Ala Trp Phe Arg Gln Ala Pro Gly Lys Glu Arg Glu Gly Val
         35                  40                  45

Ser Cys Arg Ala Ser Asp Gly Asn Thr Tyr Tyr Ala Glu Ser Leu Lys
 50                  55                  60

Gly Arg Leu Thr Met Ser Thr Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala Ser Trp Val Ala Ser Leu Trp Ser Pro Ser Glu Tyr Asp Tyr
             100                 105                 110

Trp Gly Gln Gly Thr Gln Val Thr Val Ser Ser
             115                 120
```

<210> SEQ ID NO 124
<211> LENGTH: 114
<212> TYPE: PRT
<213> ORGANISM: Artificial Sequence
<220> FEATURE:
<223> OTHER INFORMATION: Full length VHH

<400> SEQUENCE: 124

```
Gln Val Gln Leu Val Glu Ser Gly Gly Gly Leu Val Gln Pro Gly Gly
 1               5                   10                  15

Ser Leu Arg Leu Ser Cys Ala Ala Ser Gly Ser Phe Phe Ser Arg Tyr
             20                  25                  30

Arg Met Gly Trp Tyr Arg Gln Ala Pro Gly Glu Gln Arg Glu Leu Val
         35                  40                  45

Ala Ser Ile Ala Tyr Asp Gly Ser Thr Tyr Ala Asp Pro Val Lys
 50                  55                  60

Gly Arg Phe Thr Ile Ser Arg Asp Asn Ala Asn Thr Val His Leu Gln
 65                  70                  75                  80

Met Tyr Ser Leu Lys Pro Asp Asp Thr Ala Val Tyr Tyr Cys Asn Leu
                 85                  90                  95
```

-continued

Asp Pro Pro Gly Ile Leu Tyr Trp Gly Gln Gly Thr Gln Val Thr Val
            100                 105                 110
Ser Ser

<210> SEQ ID NO 125
<211> LENGTH: 125
<212> TYPE: PRT
<213> ORGANISM: Artificial Sequence
<220> FEATURE:
<223> OTHER INFORMATION: Full length VHH

<400> SEQUENCE: 125

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Gly Ala Tyr
            20                  25                  30

Ala Ile Ala Trp Phe Arg Gln Ala Pro Gly Lys Glu Arg Glu Gly Val
        35                  40                  45

Ser Cys Ile Ser Pro Ser Asp Ser Phe Thr Glu Tyr Gly Asp Ser Val
    50                  55                  60

Lys Gly Arg Phe Thr Val Ser Arg Asp Asn Ala Lys Asn Thr Val Tyr
65                  70                  75                  80

Leu Gln Met Asn Ser Leu Gln Pro Glu Asp Thr Ala Val Tyr Tyr Cys
                85                  90                  95

Ala Ala Asp Pro Val Cys Thr Ala Gly Trp Tyr Arg Pro Ser Arg Phe
            100                 105                 110

Asp Leu Trp Gly Gln Gly Thr Gln Val Thr Val Ser Ser
        115                 120                 125

<210> SEQ ID NO 126
<211> LENGTH: 117
<212> TYPE: PRT
<213> ORGANISM: Artificial Sequence
<220> FEATURE:
<223> OTHER INFORMATION: Full length VHH

<400> SEQUENCE: 126

Gln Val Gln Leu Val Glu Ser Gly Gly Gly Leu Val Gln Ser Gly Gly
1               5                   10                  15

Ser Leu Arg Leu Ser Cys Ala Ala Ser Gly Ser Met Ser Arg Ile Ile
            20                  25                  30

Thr Met Gly Trp Tyr Arg Gln Ala Pro Gly Met Glu Arg Glu Leu Val
        35                  40                  45

Ala Val Ile Gly Asn Asn Asp Asn Thr Val Tyr Gly Asp Ser Val Gln
    50                  55                  60

Gly Arg Phe Thr Val Ser Arg Asp Asn Ala Lys Asn Thr Ala Tyr Leu
65                  70                  75                  80

Gln Met Asn Ser Leu Asn Ala Glu Asp Thr Ala Met Tyr Tyr Cys Lys
                85                  90                  95

Ile Ser Thr Leu Thr Pro Pro His Glu Tyr Trp Gly Gln Gly Thr Gln
            100                 105                 110

Val Thr Val Ser Ser
        115

<210> SEQ ID NO 127
<211> LENGTH: 123
<212> TYPE: PRT
<213> ORGANISM: Artificial Sequence
<220> FEATURE:
<223> OTHER INFORMATION: Full length VHH

<400> SEQUENCE: 127

Gln Val Gln Leu Val Glu Ser Gly Gly Gly Leu Val Gln Ala Gly Asp
1               5                   10                  15

Ser Leu Arg Leu Ser Cys Thr Ala Ser Val Leu Thr Phe Ser Leu Tyr
            20                  25                  30

Arg Val Gly Trp Phe Arg Gln Ala Pro Gly Lys Glu Arg Glu Phe Val
        35                  40                  45

Ala Ala Ile Asp Trp Gly Asp Gly Pro Thr Thr Tyr Ala Asp Ser Val
    50                  55                  60

Lys Gly Arg Phe Thr Ile Ser Arg Asp Asn Ala Glu Arg Thr Ala Tyr
65                  70                  75                  80

Leu Gln Ile Asn Ser Leu Lys Pro Glu Asp Thr Ala Val Tyr Tyr Cys
                85                  90                  95

Gly Ala Gly Asn Thr Gly Ser Ser Asp Arg Ser Ser Ser Tyr Val His
            100                 105                 110

Trp Gly Gln Gly Thr Gln Val Thr Val Ser Ser
        115                 120

<210> SEQ ID NO 128
<211> LENGTH: 117
<212> TYPE: PRT
<213> ORGANISM: Artificial Sequence
<220> FEATURE:
<223> OTHER INFORMATION: Full length VHH

<400> SEQUENCE: 128

Gln Leu Gln Leu Val Glu Ser Gly Gly Gly Leu Val Gln Pro Gly Gly
1               5                   10                  15

Ser Leu Arg Leu Ser Cys Thr Ala Ser Gly Asp Ile Phe Val Met Tyr
            20                  25                  30

Met Ile Asp Trp Tyr Arg Gln Ala Pro Gly Lys Gln Arg Glu Leu Val
        35                  40                  45

Ala Ser Ile Asp Gly Arg Gly Thr Pro Met Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Ser Cys His
                85                  90                  95

Ala Lys Ser Pro Leu Val Asp Asn Glu Tyr Trp Gly Gln Gly Thr Gln
            100                 105                 110

Val Thr Val Ser Ser
        115

<210> SEQ ID NO 129
<211> LENGTH: 128
<212> TYPE: PRT
<213> ORGANISM: Artificial Sequence
<220> FEATURE:
<223> OTHER INFORMATION: Full length VHH

<400> SEQUENCE: 129

Gln Leu Gln Leu Ala Glu Ser Gly Gly Gly Leu Val Gln Ala Gly Gly
1               5                   10                  15

Ser Leu Arg Leu Ser Cys Ala Ala Ser Gly Ser Thr Leu Asn Asn Asn
            20                  25                  30

Ala Ile Gly Trp Phe Arg Gln Ala Pro Gly Lys Glu Arg Glu Gly Val
            35                  40                  45

Ser Cys Met Asn Ser Arg Asp Gly Thr Thr Asn Tyr Ala Asp Ser Val
 50                  55                  60

Lys Gly Arg Phe Thr Ile Ser Arg Asp Val Ala Lys Asn Thr Val Tyr
 65                  70                  75                  80

Leu Gln Met Asn Ser Leu Lys Pro Glu Asp Thr Ala Val Tyr Phe Cys
                 85                  90                  95

Ala Val Lys Gly Phe Ala Pro Phe Leu Ile Gly Cys Pro Trp Gly Lys
            100                 105                 110

Ala Glu Tyr Asp Tyr Trp Gly Gln Gly Thr Gln Val Thr Val Ser Ser
        115                 120                 125

<210> SEQ ID NO 130
<211> LENGTH: 123
<212> TYPE: PRT
<213> ORGANISM: Artificial Sequence
<220> FEATURE:
<223> OTHER INFORMATION: Full length VHH

<400> SEQUENCE: 130

Gln Val Gln Leu Val Glu Ser Gly Gly Gly Leu Val Gln Pro Gly Gly
 1               5                  10                  15

Ser Leu Arg Leu Ser Cys Ala Ala Ser Gly Ser Ala Phe Ser Ile Asn
             20                  25                  30

Ala Met Gly Trp Tyr Arg Gln Ala Pro Gly Glu Glu Arg Glu Phe Val
            35                  40                  45

Ala Ala Ile Thr Ala Gly Gly Asn Thr Tyr Tyr Ala Asp Ser Ala Lys
 50                  55                  60

Ala Arg Phe Thr Ile Ser Arg Asp Asn Ala Lys Asn Met Leu Tyr Leu
 65                  70                  75                  80

Gln Met Asn Ser Leu Lys Pro Glu Asp Thr Ala Met Tyr Tyr Cys Ala
                 85                  90                  95

Ala Thr Lys Ala Phe Gly Ile Ala Thr Ile Thr Ala Asp Tyr Glu Leu
            100                 105                 110

Trp Gly Gln Gly Thr Gln Val Thr Val Ser Ser
        115                 120

<210> SEQ ID NO 131
<211> LENGTH: 117
<212> TYPE: PRT
<213> ORGANISM: Artificial Sequence
<220> FEATURE:
<223> OTHER INFORMATION: Full length VHH

<400> SEQUENCE: 131

Gln Val Gln Leu Val Glu Ser Gly Gly Gly Leu Val Gln Pro Gly Gly
 1               5                  10                  15

Ser Leu Arg Leu Ser Cys Ser Ala Ser Gly Ser Ile Ser Ser Ile Val
             20                  25                  30

Thr Met Gly Trp Tyr Arg Gln Ala Pro Gly Lys Glu Arg Glu Leu Val
            35                  40                  45

Ala Val Ile Gly Asn Tyr Gly Asn Thr Asn Tyr Ala Asp Ser Val Lys
 50                  55                  60

Gly Arg Phe Thr Val Ser Arg Asp Asn Ala Lys Asn Thr Val Tyr Leu
 65                  70                  75                  80

```
Gln Met Asn Ser Leu Asn Val Glu Asp Thr Ala Met Tyr Val Cys Lys
            85                  90                  95

Phe Ser Ser Thr Val Ala Pro His Glu Tyr Trp Gly Gly Thr Gln
            100                 105                 110

Val Thr Val Ser Ser
        115

<210> SEQ ID NO 132
<211> LENGTH: 116
<212> TYPE: PRT
<213> ORGANISM: Artificial Sequence
<220> FEATURE:
<223> OTHER INFORMATION: Full length VHH

<400> SEQUENCE: 132

Gln Val Gln Leu Val Glu Ser Gly Gly Gly Leu Val Gln Pro Gly Gly
1               5                   10                  15

Ser Leu Arg Leu Ser Cys Ala Ala Ser Asp Asn Ile Phe Ser Phe Tyr
            20                  25                  30

Thr Met Gly Trp Tyr Arg Gln Ser Pro Gly Lys Glu Arg Glu Leu Val
            35                  40                  45

Ala Val Ile Gly Asn Gly Gly Asn Thr Asn Tyr Ala Asp Ser Val Lys
        50                  55                  60

Gly Arg Phe Thr Ile Ser Arg Asp Asn Gly Lys Asn Lys Ala His Leu
65                  70                  75                  80

Gln Met Asn Ser Leu Lys Pro Glu Asp Thr Ala Val Tyr Tyr Cys Lys
            85                  90                  95

Ala Ser Gly Pro Gly Gly Val Glu Val Trp Gly Gln Gly Thr Gln Val
            100                 105                 110

Thr Val Ser Ser
        115

<210> SEQ ID NO 133
<211> LENGTH: 116
<212> TYPE: PRT
<213> ORGANISM: Artificial Sequence
<220> FEATURE:
<223> OTHER INFORMATION: Full length VHH

<400> SEQUENCE: 133

Gln Val Gln Leu Val Glu Ser Gly Gly Gly Leu Val Gln Pro Gly Gly
1               5                   10                  15

Ser Leu Arg Leu Ser Cys Ala Ala Ser Thr Asn Ile Ala Ser Phe Tyr
            20                  25                  30

Thr Met Gly Trp Tyr Arg Gln Thr Pro Gly Gln Gln Arg Asp Val Val
            35                  40                  45

Ala Val Ile Gly Asn Gly Gly Asn Thr Asn Tyr Ala Asp Ser Val Lys
        50                  55                  60

Gly Arg Phe Thr Ile Ser Arg Asp Gly Ala Lys Asn Thr Ala His Leu
65                  70                  75                  80

Gln Met Asn Ser Leu Lys Pro Glu Asp Thr Asp Val Tyr Tyr Cys Lys
            85                  90                  95

Ala Ser Gly Pro Gly Gly Val Ile Leu Trp Gly Gln Gly Thr Gln Val
            100                 105                 110

Thr Val Ser Ser
        115
```

INFLUENZA VIRUS ANTIBODY COMPOSITIONS

CROSS-REFERENCE TO RELATED APPLICATIONS

This application is the National Stage of International Application No. PCT/GB2012/052164, filed Sep. 3, 2012, which claims the benefit of Great Britain application number GB1115214.7, filed Sep. 2, 2011, the disclosures of which are incorporated herein by reference in their entireties.

The present invention relates to antibody compositions, and to the use thereof for preventing or treating influenza infection. The present invention also relates to the use of said antibody compositions for assessing cross-reactivity and haemagglutinin antigen content of influenza vaccines in vaccine potency assays.

The emergence of highly pathogenic influenza viral strains poses a serious threat to public health on a global scale. Although vaccines are the mainstay of infection, controlling the gap between the emergence of new viral strains and a clinically approved vaccine presents a serious concern particularly as resistance to existing anti-viral drugs like OSELTAMAVIR™ and ZANAMIVIR™ is increasing.

One current approach is passive immunotherapy with serum from convalescent patients. This approach, however, has major limitations to population-wide implementation, such as prohibitive cost, high risk of toxicity, uncertain dosing, and difficulty in administration.

Another approach is to stockpile recombinant monoclonal antibodies for immediate deployment on emergence of a new pandemic threat. By way of example, recent reports have described the isolation of functional human antibodies from survivors of the 1918 influenza pandemic (Kashyap et al., 2008), from seasonal vaccinated individuals (Ekiert et al., 2009), and from naive human antibody libraries (Sui et al., 2009). However, although conventional monoclonal antibodies are generally regarded as a successful class of drug, their high cost and complexity is a major limitation. Also, in view of the rapidly changing epidemiology of influenza virus, such monoclonal antibody approach would necessitate the provision of a monoclonal antibody that demonstrates reactivity across different viral sub-types. This problem currently presents a major challenge for monoclonal antibody technology.

Pandemic influenza occurs when a new virus emerges and infects a global human population that has little or no pre-existing immunity. The most recent H1N1 2009 pandemic, although a considerable economic burden, did not result in the same rates of mortality as previous pandemics like the 1918 'Spanish flu' pandemic, which resulted in an estimated 50 million deaths worldwide. Highly pathogenic avian H5N1 influenza viruses have demonstrated mortality rates of 60% in infected humans and clearly highlight the risk that pandemic influenza presents.

Current treatment options fall into two categories; either anti-viral drugs or vaccines. Current anti-viral drugs target either the viral neuraminidase (e.g. OSELTAMAVIR™) or the M2 ion channel (e.g. AMANTADINE™); both of which may become ineffective in time due to increasing resistance. Vaccines are the corner stone of infection control, but have limitations in that it takes significant time to develop a vaccine upon emergence of a new viral strain, they do not act quickly, they are not effective in all population groups (e.g. immune-compromised patients), protection is largely strain-specific, and there is limited world-wide production capacity. Thus, there is clearly a need for additional treatment options.

Another problem in the art is a need for the standardisation and control of both seasonal and pandemic influenza vaccines. Currently, the single radial immunodiffusion assay (SRD) is considered a 'gold-standard' test to determine the content of HA antigen in influenza vaccines. This assay requires the development of reference antiserum to each new viral strain, which may typically add 2-3 months to the vaccine development pipeline. Naturally, the elimination of this delay would be invaluable in mounting a rapid response to a pandemic emergency. To this end, there is a need for a 'universal antibody' reagent, which comprises cross-reactive antibodies that may be used in a SRD assay or in other related assay formats based on for example, ELISA, Surface Plasmon Resonance (SPR) or mass spectrometry.

There is therefore an urgent need for alternative influenza virus treatment options, for a robust influenza virus detection assay, and/or for an influenza virus antigen-based vaccine potency assay.

The present invention addresses one or more of the above problems by providing an antibody as described herein.

A principal feature of the antibodies of the present invention is that they possess a complementary determining region (CDR), for example a CDR3 amino acid sequence, from an alpaca $V_{HH}$ single-domain antibody.

In one embodiment, the present invention comprises or consists of a single-domain camelid (e.g. an alpaca single-domain antibody)—said antibodies have a very simple and robust protein scaffold, and demonstrate several advantages over conventional monoclonal antibodies, such as: (i) size—single-domain antibodies are approximately $1/10^{th}$ the size of monoclonal antibodies. As a result, said antibodies have the ability to access buried or hidden epitopes that would normally be silent to the human immune system (eg. accessing more conserved epitopes buried in the haemagglutinin stalk region); (ii) production at significantly lower cost than conventional monoclonal antibodies; (iii) simpler methods to engineer into bi- or multi-specific antibodies; (iv) longer CDR3 loops than conventional antibodies, which facilitates more adept accessing of clefts and grooves on antigenic surfaces; and/or (v) high structural stability.

In one embodiment, an antibody of the invention binds to a H1 influenza virus (e.g. a H1N1 influenza virus), for example a pandemic H1 (e.g. H1N1) influenza virus. In one embodiment, the antibody binds to strain A/California/06/09 and/or A/California/07/2009 and/or A/Brisbane/59/2007.

In one embodiment an antibody of the invention has a CDR3, which comprises an amino acid sequence selected from the group consisting of: SEQ ID NO: 1-19; or a variant amino acid sequence thereof, wherein said variant amino acid sequence possesses a maximum of 1 or 2 amino acid substitution, deletion or insertion when compared with the corresponding amino acid sequence of SEQ ID NO: 1-19. In this regard, SEQ ID NOs 1-19 are defined according to the conventional Kabat nomenclature.

In another embodiment an antibody of the invention has a CDR3, which comprises an amino acid sequence selected from the group consisting of: SEQ ID NO: 20-38; or a variant amino acid sequence thereof, wherein said variant amino acid sequence possesses a maximum of 1 or 2 amino acid substitution, deletion or insertion when compared with the corresponding amino acid sequence of SEQ ID NO: 20-38. In this regard, SEQ ID NOs 20-38 are defined according to the conventional international ImMunoGeneTics information system for immunoglobulins or antibodies (IMGT) nomenclature.

An antibody of the invention may further include a CDR2, wherein said CDR2 comprises an amino acid sequence selected from the group consisting of: SEQ ID NO: 39-57; or a variant amino acid sequence thereof, wherein said variant amino acid sequence possesses a maximum of 1 or 2 amino acid substitution, deletion or insertion when compared with the corresponding amino acid sequence of SEQ ID NO: 39-57. In this regard, SEQ ID NOs 39-57 are defined according to conventional Kabat nomenclature. Alternatively, said CDR2 comprises an amino acid sequence selected from the group consisting of: SEQ ID NO: 58-76; or a variant amino acid sequence thereof, wherein said variant amino acid sequence possesses a maximum of 1 or 2 amino acid substitution, deletion or insertion when compared with the corresponding amino acid sequence of SEQ ID NO: 58-76. In this regard, SEQ ID NOs 58-78 are defined according to conventional IMGT nomenclature.

Simply by way of illustration, an antibody of the invention may comprise CDR 3 and CDR2 combinations as hereinbefore defined based on the following combinations of SEQ ID NOs:

1 plus 39 or 58; 20 plus 39 or 58;
2 plus 40 or 59; 21 plus 40 or 59;
3 plus 41 or 60; 22 plus 41 or 60;
4 plus 42 or 61; 23 plus 42 or 61;
5 plus 43 or 62; 24 plus 43 or 62;
6 plus 44 or 63; 25 plus 44 or 63;
7 plus 45 or 64; 26 plus 45 or 64;
8 plus 46 or 65; 27 plus 46 or 65;
9 plus 47 or 66; 28 plus 47 or 66;
10 plus 48 or 67; 29 plus 48 or 67;
11 plus 49 or 68; 30 plus 49 or 68;
12 plus 50 or 69; 31 plus 50 or 69;
13 plus 51 or 70; 32 plus 51 or 70;
14 plus 52 or 71; 33 plus 52 or 71;
15 plus 53 or 72; 34 plus 53 or 72;
16 plus 54 or 73; 35 plus 54 or 73;
17 plus 55 or 74; 36 plus 55 or 74;
18 plus 56 or 75; 37 plus 56 or 75;
19 plus 57 or 76; 38 plus 57 or 76.

In addition to the above-mention CDR3 feature (and optionally in addition to the above-mentioned CDR2 feature), an antibody of the invention may further include a CDR1, wherein said CDR1 comprises an amino acid sequence selected from the group consisting of: SEQ ID NO: 77-95; or a variant amino acid sequence thereof, wherein said variant amino acid sequence possesses a maximum of 1 or 2 amino acid substitution, deletion or insertion when compared with the corresponding amino acid sequence of SEQ ID NO: 77-95. In this regard, SEQ ID NOs 77-95 are defined according to conventional Kabat nomenclature. Alternatively, said CDR1 comprises an amino acid sequence selected from the group consisting of: SEQ ID NO: 96-114; or a variant amino acid sequence thereof, wherein said variant amino acid sequence possesses a maximum of 1 or 2 amino acid substitution, deletion or insertion when compared with the corresponding amino acid sequence of SEQ ID NO: 96-114. In this regard, SEQ ID NOs 96-114 are defined according to conventional IMGT nomenclature.

Simply by way of illustration, an antibody of the invention may comprise CDR3 and CDR1 combinations as hereinbefore defined based on the following combinations of SEQ ID NOs:

1 plus 77 or 96; 20 plus 77 or 96;
2 plus 78 or 97; 21 plus 78 or 97;
3 plus 79 or 98; 22 plus 79 or 98;
4 plus 80 or 99; 23 plus 80 or 99;
5 plus 81 or 100; 24 plus 81 or 100;
6 plus 82 or 101; 25 plus 82 or 101;
7 plus 83 or 102; 26 plus 83 or 102;
8 plus 84 or 103; 27 plus 84 or 103;
9 plus 85 or 104; 28 plus 85 or 104;
10 plus 86 or 105; 29 plus 86 or 105;
11 plus 87 or 106; 30 plus 87 or 106;
12 plus 88 or 107; 31 plus 88 or 107;
13 plus 89 or 108; 32 plus 89 or 108;
14 plus 90 or 109; 33 plus 90 or 109;
15 plus 91 or 110; 34 plus 91 or 110;
16 plus 92 or 111; 35 plus 92 or 111;
17 plus 93 or 112; 36 plus 93 or 112;
18 plus 94 or 113; 37 plus 94 or 113;
19 plus 95 or 114; 38 plus 95 or 114.

Again, simply by way of illustration, an antibody of the invention may comprise CDR3 plus CDR2 and CDR1 combinations as hereinbefore defined based on the following combinations of SEQ ID NOs:

1 plus 39 plus 77; 20 plus 58 plus 96;
2 plus 40 plus 78; 21 plus 59 plus 97;
3 plus 41 plus 79; 22 plus 60 plus 98;
4 plus 42 plus 80; 23 plus 61 plus 99;
5 plus 43 plus 81; 24 plus 62 plus 100;
6 plus 44 plus 82; 25 plus 63 plus 101;
7 plus 45 plus 83; 26 plus 64 plus 102;
8 plus 46 plus 84; 27 plus 65 plus 103;
9 plus 47 plus 85; 28 plus 66 plus 104;
10 plus 48 plus 86; 29 plus 67 plus 105;
11 plus 49 plus 87; 30 plus 68 plus 106;
12 plus 50 plus 88; 31 plus 69 plus 107;
13 plus 51 plus 89; 32 plus 70 plus 108;
14 plus 52 plus 90; 33 plus 71 plus 109;
15 plus 53 plus 91; 34 plus 72 plus 110;
16 plus 54 plus 92; 35 plus 73 plus 111;
17 plus 55 plus 93; 36 plus 74 plus 112;
18 plus 56 plus 94; 37 plus 75 plus 113;
19 plus 57 plus 95; 38 plus 76 plus 114.

In one embodiment, an antibody of the invention comprises an amino acid sequence having at least 80% sequence identity to an amino acid sequence selected from the group consisting of SEQ ID NOs: 115-133. In a related embodiment, said antibody retains the precise CDR3 amino acid sequence as herein before defined, and optionally the precise CDR1 amino acid sequence and/or precise CDR2 amino acid sequence as hereinbefore defined.

In a related second aspect, an antibody of the invention binds not only to H1 influenza virus (as hereinbefore described) but also to a H5 influenza virus (e.g. H5N1 or H5N3), for example a pandemic H5 influenza virus. In one embodiment, the antibody binds to strain A/Vietnam/1203/2004 and/or A/Vietnam/1194/2004 and/or A/Vietnam/119/2004 and/or A/HongKong/213/2003 and/or A/turkey/Turkey/1/2005 and/or A/Indonesia/05/2005 and/or A/Duck/Singapore-Q/119-3/97. In one embodiment of this aspect, an antibody of the invention has a CDR3, which comprises an amino acid sequence selected from the group consisting of: SEQ ID NO: 3-4, 6-7, 10, 13 or 15; or a variant amino acid sequence thereof, wherein said variant amino acid sequence possesses a maximum of 1 or 2 amino acid substitution, deletion or insertion when compared with the corresponding amino acid sequence of SEQ ID NO: 3-4, 6-7, 10, 13 or 15. Alternatively, said CDR3 comprises an amino acid sequence selected from the group consisting of: SEQ ID NO: 22-23, 25-26, 29, 32 or 34; or a variant amino acid sequence thereof, wherein said variant amino acid sequence possesses a maximum of 1 or 2 amino acid substitution, deletion or insertion when compared with the corresponding amino acid sequence of SEQ ID NO: 22-23, 25-26, 29, 32 or 34.

An antibody of the second aspect may further include a CDR2, wherein said CDR2 comprises an amino acid sequence selected from the group consisting of: SEQ ID NO: 41-42, 44-45, 48, 51 or 53; or a variant amino acid sequence thereof, wherein said variant amino acid sequence possesses a maximum of 1 or 2 amino acid substitution, deletion or insertion when compared with the corresponding amino acid sequence of SEQ ID NO: 41-42, 44-45, 48, 51 or 53. Alternatively, said CDR2 comprises an amino acid sequence selected from the group consisting of: SEQ ID NO: 60-61, 63-64, 67, 70 or 72; or a variant amino acid sequence thereof, wherein said variant amino acid sequence possesses a maximum of 1 or 2 amino acid substitution, deletion or insertion when compared with the corresponding amino acid sequence of SEQ ID NO: 60-61, 63-64, 67, 70 or 72.

Simply by way of illustration, an antibody of the second aspect may comprise CDR 3 and CDR2 combinations as hereinbefore defined for the second aspect based on the following combinations of SEQ ID NOs:
   3 plus 41 or 60; 22 plus 41 or 60;
   4 plus 42 or 61; 23 plus 42 or 61;
   6 plus 44 or 63; 25 plus 44 or 63;
   7 plus 45 or 64; 26 plus 45 or 64;
   10 plus 48 or 67; 29 plus 48 or 67;
   13 plus 51 or 70; 32 plus 51 or 70;
   15 plus 53 or 72; 34 plus 53 or 72.

An antibody of the second aspect, in addition to the above-mention CDR3 feature (and optionally in addition to the above-mentioned CDR2 feature), may further include a CDR1, wherein said CDR1 comprises an amino acid sequence selected from the group consisting of: SEQ ID NO: 79-80, 82-83, 86, 89 or 91; or a variant amino acid sequence thereof, wherein said variant amino acid sequence possesses a maximum of 1 or 2 amino acid substitution, deletion or insertion when compared with the corresponding amino acid sequence of SEQ ID NO: 79-80, 82-83, 86, 89 or 91. Alternatively, said CDR1 comprises an amino acid sequence selected from the group consisting of: SEQ ID NO: 98-99, 101-102, 105, 108 or 110; or a variant amino acid sequence thereof, wherein said variant amino acid sequence possesses a maximum of 1 or 2 amino acid substitution, deletion or insertion when compared with the corresponding amino acid sequence of SEQ ID NO: 98-99, 101-102, 105, 108 or 110.

Simply by way of illustration, an antibody of the second aspect may comprise CDR3 and CDR1 combinations as hereinbefore defined for the second aspect based on the following combinations of SEQ ID NOs:
   3 plus 79 or 98; 22 plus 79 or 98;
   4 plus 80 or 99; 23 plus 80 or 99;
   6 plus 82 or 101; 25 plus 82 or 101;
   7 plus 83 or 102; 26 plus 83 or 102;
   10 plus 86 or 105; 29 plus 86 or 105;
   13 plus 89 or 108; 32 plus 89 or 108;
   15 plus 91 or 110; 34 plus 91 or 110.

Again, simply by way of illustration, an antibody of the second aspect may comprise CDR3 plus CDR2 and CDR1 combinations as hereinbefore defined for the second aspect based on the following combinations of SEQ ID NOs:
   3 plus 41 plus 79; 22 plus 60 plus 98;
   4 plus 42 plus 80; 23 plus 61 plus 99;
   6 plus 44 plus 82; 25 plus 63 plus 101;
   7 plus 45 plus 83; 26 plus 64 plus 102;
   10 plus 48 plus 86; 29 plus 67 plus 105;
   13 plus 51 plus 89; 32 plus 70 plus 108
   15 plus 53 plus 91; 34 plus 72 plus 110.

An antibody of the second aspect may comprise an amino acid sequence having at least 80% sequence identity to an amino acid sequence selected from the group consisting of SEQ ID NOs: 117-118, 120-121, 124, 127 or 129. In a related embodiment, said antibody retains the precise CDR3 amino acid sequence as herein before defined, and optionally the precise CDR1 amino acid sequence and/or precise CDR2 amino acid sequence as hereinbefore defined.

In a related third aspect, an antibody of the invention binds not only to a H1 influenza virus and to a H5 influenza virus (as hereinbefore described), but also to 1) a H2 influenza virus (e.g. H2N2 or H2N3) such as to a pandemic H2 influenza virus (e.g. H2N2 or H2N3), and to 2) a H9 influenza virus (e.g. H9N2) such as to a pandemic H9 influenza virus (e.g. H9N2). For example, the antibody binds to H2 influenza virus strain A/Japan/305/1957 and/or to A/Mallard/Eng/727/06. For example, the antibody binds to H9 influenza virus strain A/HongKong/1073/99. In one embodiment of this aspect, an antibody of the invention has a CDR3, which comprises an amino acid sequence selected from the group consisting of: SEQ ID NO: 3, 4, 7 or 10; or a variant amino acid sequence thereof, wherein said variant amino acid sequence possesses a maximum of 1 or 2 amino acid substitution, deletion or insertion when compared with the corresponding amino acid sequence of SEQ ID NO: 3, 4, 7 or 10. Alternatively, said CDR3 comprises an amino acid sequence selected from the group consisting of: SEQ ID NO: 22, 23, 26 or 29; or a variant amino acid sequence thereof, wherein said variant amino acid sequence possesses a maximum of 1 or 2 amino acid substitution, deletion or insertion when compared with the corresponding amino acid sequence of SEQ ID NO: 22, 23, 26 or 29.

An antibody of the third aspect may further include a CDR2, wherein said CDR2 comprises an amino acid sequence selected from the group consisting of: SEQ ID NO: 41, 42, 45 or 48; or a variant amino acid sequence thereof, wherein said variant amino acid sequence possesses a maximum of 1 or 2 amino acid substitution, deletion or insertion when compared with the corresponding amino acid sequence of SEQ ID NO: 41, 42, 45 or 48. Alternatively, said CDR2 comprises an amino acid sequence selected from the group consisting of: SEQ ID NO: 60, 61, 64 or 67; or a variant amino acid sequence thereof, wherein said variant amino acid sequence possesses a maximum of 1 or 2 amino acid substitution, deletion or insertion when compared with the corresponding amino acid sequence of SEQ ID NO: 60, 61, 64 or 67.

Simply by way of illustration, an antibody of the third aspect may comprise CDR 3 and CDR2 combinations as hereinbefore defined for the third aspect based on the following combinations of SEQ ID NOs:
   3 plus 41 or 60; 22 plus 41 or 60;
   4 plus 42 or 61; 23 plus 42 or 61;
   7 plus 45 or 64; 26 plus 45 or 64;
   10 plus 48 or 67; 29 plus 48 or 67.

An antibody of the third aspect, in addition to the above-mention CDR3 feature (and optionally in addition to the above-mentioned CDR2 feature), may further include a CDR1, wherein said CDR1 comprises an amino acid sequence selected from the group consisting of: SEQ ID NO: 79, 80, 83 or 86; or a variant amino acid sequence thereof, wherein said variant amino acid sequence possesses a maximum of 1 or 2 amino acid substitution, deletion or insertion when compared with the corresponding amino acid sequence of SEQ ID NO: 79, 80, 83 or 86. Alternatively, said CDR1 comprises an amino acid sequence selected from the group consisting of: SEQ ID NO: 98, 99, 102 or 105; or a variant amino acid sequence thereof, wherein said variant amino acid sequence possesses a maximum of 1 or 2 amino acid substitution, deletion or insertion when compared with the corresponding amino acid sequence of SEQ ID NO: 98, 99, 102 or 105.

Simply by way of illustration, an antibody of the third aspect may comprise CDR3 and CDR1 combinations as hereinbefore defined for the third aspect based on the following combinations of SEQ ID NOs:

3 plus 79 or 98; 22 plus 79 or 98;
4 plus 80 or 99; 23 plus 80 or 99;
7 plus 83 or 102; 26 plus 83 or 102;
10 plus 86 or 105; 29 plus 86 or 105.

Again, simply by way of illustration, an antibody of the third aspect may comprise CDR3 plus CDR2 and CDR1 combinations as hereinbefore defined for the third aspect based on the following combinations of SEQ ID NOs:

3 plus 41 plus 79; 22 plus 60 plus 98;
4 plus 42 plus 80; 23 plus 61 plus 99;
7 plus 45 plus 83; 26 plus 64 plus 102;
10 plus 48 plus 86; 29 plus 67 plus 105;
15 plus 53 plus 91; 34 plus 72 plus 110.

An antibody of the third aspect may comprise an amino acid sequence having at least 80% sequence identity to an amino acid sequence selected from the group consisting of SEQ ID NOs: 117, 118, 121 or 124. In a related embodiment, said antibody retains the precise CDR3 amino acid sequence as herein before defined, and optionally the precise CDR1 amino acid sequence and/or precise CDR2 amino acid sequence as hereinbefore defined.

In a related fourth aspect, an antibody of the invention binds not only to a H1 influenza virus and to a H5 influenza virus (as hereinbefore described), but also to a H2 influenza virus (e.g. H2N2 or H2N3) for example to a pandemic H2 influenza virus (e.g. H2N2 or H2N3). By way of a specific H2 influenza virus example, the antibody binds to strain A/Japan/305/1957 and/or to A/Mallard/Eng/727/06. In one embodiment of this aspect, an antibody of the invention has a CDR3, which comprises an amino acid sequence selected from the group consisting of: SEQ ID NO: 6 or 15; or a variant amino acid sequence thereof, wherein said variant amino acid sequence possesses a maximum of 1 or 2 amino acid substitution, deletion or insertion when compared with the corresponding amino acid sequence of SEQ ID NO: 6 or 15. Alternatively, said CDR3 comprises an amino acid sequence selected from the group consisting of: SEQ ID NO: 25 or 34; or a variant amino acid sequence thereof, wherein said variant amino acid sequence possesses a maximum of 1 or 2 amino acid substitution, deletion or insertion when compared with the corresponding amino acid sequence of SEQ ID NO: 25 or 34.

An antibody of the fourth aspect may further include a CDR2, wherein said CDR2 comprises an amino acid sequence selected from the group consisting of: SEQ ID NO: 44 or 53; or a variant amino acid sequence thereof, wherein said variant amino acid sequence possesses a maximum of 1 or 2 amino acid substitution, deletion or insertion when compared with the corresponding amino acid sequence of SEQ ID NO: 44 or 53. Alternatively, said CDR2 comprises an amino acid sequence selected from the group consisting of: SEQ ID NO: 63 or 72; or a variant amino acid sequence thereof, wherein said variant amino acid sequence possesses a maximum of 1 or 2 amino acid substitution, deletion or insertion when compared with the corresponding amino acid sequence of SEQ ID NO: 63 or 72.

Simply by way of illustration, an antibody of the fourth aspect may comprise CDR3 and CDR2 combinations as hereinbefore defined for the fourth aspect based on the following combinations of SEQ ID NOs:

6 plus 44 or 63; 25 plus 44 or 63;
15 plus 53 or 61; 34 plus 53 or 61.

An antibody of the fourth aspect, in addition to the above-mention CDR3 feature (and optionally in addition to the above-mentioned CDR2 feature), may further include a CDR1, wherein said CDR1 comprises an amino acid sequence selected from the group consisting of: SEQ ID NO: 82 or 91; or a variant amino acid sequence thereof, wherein said variant amino acid sequence possesses a maximum of 1 or 2 amino acid substitution, deletion or insertion when compared with the corresponding amino acid sequence of SEQ ID NO: 62 or 91. Alternatively, said CDR1 comprises an amino acid sequence selected from the group consisting of: SEQ ID NO: 101 or 110; or a variant amino acid sequence thereof, wherein said variant amino acid sequence possesses a maximum of 1 or 2 amino acid substitution, deletion or insertion when compared with the corresponding amino acid sequence of SEQ ID NO: 101 or 110.

Simply by way of illustration, an antibody of the fourth aspect may comprise CDR3 and CDR1 combinations as hereinbefore defined for the fourth aspect based on the following combinations of SEQ ID NOs:

6 plus 82 or 101; 25 plus 82 or 101;
15 plus 91 or 110; 34 plus 91 or 110.

Again, simply by way of illustration, an antibody of the fourth aspect may comprise CDR3 plus CDR2 and CDR1 combinations as hereinbefore defined for the fourth aspect based on the following combinations of SEQ ID NOs:

6 plus 44 plus 82; 25 plus 63 plus 101;
15 plus 53 plus 91; 34 plus 72 plus 110.

An antibody of the fourth aspect may comprise an amino acid sequence having at least 80% sequence identity to an amino acid sequence selected from the group consisting of SEQ ID NOs: 120 or 129. In a related embodiment, said antibody retains the precise CDR3 amino acid sequence as herein before defined, and optionally the precise CDR1 amino acid sequence and/or precise CDR2 amino acid sequence as hereinbefore defined.

In a related fifth aspect, an antibody of the invention binds not only to a H1 influenza virus and to a H5 influenza virus (as hereinbefore described), but also to a H9 influenza virus (e.g. H9N2) for example to a pandemic H9 influenza virus (e.g. H9N2). By way of a specific H9 influenza virus example, the antibody binds to strain A/HongKong/1073/99. In one embodiment of this aspect, an antibody of the invention has a CDR3, which comprises an amino acid sequence selected from the group consisting of: SEQ ID NO: 13; or a variant amino acid sequence thereof, wherein said variant amino acid sequence possesses a maximum of 1 or 2 amino acid substitution, deletion or insertion when compared with the corresponding amino acid sequence of SEQ ID NO: 13. Alternatively, said CDR3 comprises an amino acid sequence selected from the group consisting of: SEQ ID NO: 32; or a variant amino acid sequence thereof, wherein said variant amino acid sequence possesses a maximum of 1 or 2 amino acid substitution, deletion or insertion when compared with the corresponding amino acid sequence of SEQ ID NO: 32.

An antibody of the fifth aspect may further include a CDR2, wherein said CDR2 comprises an amino acid sequence selected from the group consisting of: SEQ ID NO: 51 or 70; or a variant amino acid sequence thereof, wherein said variant amino acid sequence possesses a maximum of 1 or 2 amino acid substitution, deletion or insertion when compared with the corresponding amino acid sequence of SEQ ID NO: 51 or 70.

Simply by way of illustration, an antibody of the fifth aspect may comprise CDR3 and CDR2 combinations as hereinbefore defined for the fifth aspect based on the following combinations of SEQ ID NOs: 13 plus 51 or 70; 32 plus 51 or 70.

An antibody of the fifth aspect, in addition to the abovemention CDR3 feature (and optionally in addition to the above-mentioned CDR2 feature), may further include a CDR1, wherein said CDR1 comprises an amino acid sequence selected from the group consisting of: SEQ ID NO: 89 or 108; or a variant amino acid sequence thereof, wherein said variant amino acid sequence possesses a maximum of 1 or 2 amino acid substitution, deletion or insertion when compared with the corresponding amino acid sequence of SEQ ID NO: 89 or 108.

Simply by way of illustration, an antibody of the fifth aspect may comprise CDR3 and CDR1 combinations as hereinbefore defined for the fifth aspect based on the following combinations of SEQ ID NOs: 13 plus 89 or 108; 32 plus 89 or 108.

Again, simply by way of illustration, an antibody of the fifth aspect may comprise CDR3 plus CDR2 and CDR1 combinations as hereinbefore defined for the fifth aspect based on the following combinations of SEQ ID NOs: 13 plus 51 plus 89; 32 plus 70 plus 108.

An antibody of the fifth aspect may comprise an amino acid sequence having at least 80% sequence identity to an amino acid sequence selected from the group consisting of SEQ ID NOs: 127. In a related embodiment, said antibody retains the precise CDR3 amino acid sequence as herein before defined, and optionally the precise CDR1 amino acid sequence and/or precise CDR2 amino acid sequence as hereinbefore defined.

In one embodiment, the antibodies of the invention bind and preferably neutralise all Group I haemagglutinin influenza viruses (e.g. H1, H2, H5, H6, H11, H13, H16, H9, H8 and/or H12 influenza viruses). In one embodiment, the antibodies of the invention bind and preferably neutralise A/California/07/09 (H1N1) and/or A/Vietnam/1194/04 (H5N1).

In one embodiment, the antibody may be humanized. Examples of conventional humanization techniques are described in Jones P. T. et al. (1986) Replacing the complementarity-determining regions in a human antibody with those from a mouse; Nature, 321 (6069): pp. 522-525, which is hereby incorporated in its entirety by reference thereto. In one embodiment, the CDR3 $V_{HH}$ amino acid sequence of the present invention may be inserted (e.g. replace) a corresponding CDR3 $V_{HH}$ amino acid sequence present on a human antibody. Alternatively, the entire $V_{HH}$ amino acid sequence of an antibody of the present invention may be sequence aligned with a corresponding human antibody and amino acid differences mapped. Following said mapping, amino acid differences identified on the antibody sequence of the present invention present may then be modified to mimic the corresponding human sequence. In this regard, CDR regions are preferably not modified. For example, differences identified in the FR regions of an antibody of the present invention, optionally subject to 'Hallmark' residues (Vincke et al, 2008, J. Biol. Chem., 284(5), pp. 3273-3284), which is hereby incorporated in its entirety by reference thereto, may be modified to mimic the corresponding human sequence. Simply for illustrative purposes, one humanization protocol is described by way of Example 10.

Purely for illustrative purposes, a humanized antibody of the invention may comprise an amino acid sequence having at least 80% sequence identity to a human VH antibody, for example a human VH3 antibody such as is encoded by the VH3 germline genes DP51 or DP53.

In one embodiment, an antibody (optionally humanized) of the present invention consists or comprises a single-domain antibody.

In another embodiment, an antibody (optionally humanized) of the present invention may comprise two or more single-domains as hereinbefore defined. Said single-domains may be the same or different. When first and second (or more) different single-domains are employed, the first single-domain typically has a binding affinity, avidity and/or specificity that is different from that of the second single-domain.

In one embodiment, an antibody (optionally humanized) of the present invention consists or comprises a bi-specific or multi-specific antibody.

According to a further aspect of the present invention, there is provided an antibody as hereinbefore defined, for use in preventing or treating influenza virus infection. In a related aspect, the present invention provides a method comprising administering a prophylatically effective or therapeutically effective amount of an antibody as hereinbefore defined to a patient. These aspects include the use of two or more of said hereinbefore defined antibodies.

Typical patients benefiting from the above 'passive immunotherapy' aspect include 'at risk' individuals on emergence of a new influenza virus strain (eg. a new pandemic strain such as a new Group 1 influenza strain). Examples of such 'at risk' patients include: vaccine non-responders; immunecompromised patients; and health professionals. A particular advantage to the passive immunotherapy approach of the present invention is that it does not add to the growing problems associated with anti-viral drug resistance.

In one embodiment, the antibody or antibody combinations of the present invention provide heterosubtypic cross-reactivity and/or neutralisation against influenza H1, H1 & H5 subtypes, and/or H1 & H2 & H5 & H9 subtypes, and/or all Group I haemagglutinin subtypes (e.g. H1, H2, H5, H6, H11, H13, H16, H9, H8 and/or H12 influenza viruses).

A further aspect of the present invention provides method for designing "universal vaccine" to elicit heterosubtypic immune response. Simply for illustrative purposes, suitable protocols are described in Example 14.

A yet further aspect of the present invention provides robust 'field' diagnostic assays and reagents. Simply for illustrative purposes, suitable protocols are described in Example 13.

A further aspect of the present invention provides cross-reactive antibodies for vaccine is potency determination. Simply for illustrative purposes suitable protocols are described in Example 13.

Antibody Delivery

In use, the present invention employs a pharmaceutical composition, comprising the antibody composition of the present invention in a form suitable for parenteral, usually intravenous administration. The purified intact antibodies, or their fragments, are formulated for such delivery. For example, antibody, or its fragment, at a concentration between 5-50 or 15-50 or 25-50 g/liter may be formulated in buffer. Examples of suitable buffer components include physiological salts such as sodium citrate and/or citric acid. Preferred buffers contain 100-200 or 125-175 or approximately 150 (eg. 153) mM physiological salts such as sodium chloride. Preferred buffers maintain the pharmaceutical composition at a pH that is close to the physiological pH of the patient—for example, at a pH of 5.5-6.4, or at a pH of 5.6-6.3, or at a pH of 5.7-6.2, or at a pH of 5.8-6.2. The antibody-containing compositions of the present invention preferably exclude adjuvant(s) as it is undesirable to stimulate an immune response against said antibodies in the patient.

Antibodies of the invention may be formulated for, but not limited to intramuscular, subcutaneous, intranasal or intravenous delivery. Compositions suitable for intramuscular, subcutaneous or intravenous injection include sterile aqueous solutions. Such aqueous solutions should be suitably buffered if necessary and the liquid diluent first rendered isotonic with sufficient saline or glucose. The antibody compositions of the present invention may separately be formulated as oral formulations.

Compositions suitable for injection may be in the form of solutions, suspensions or dry powders which are dissolved or suspended in a suitable vehicle prior to use.

In preparing solutions of the antibodies or their fragments can be dissolved in the vehicle, the solution being made isotonic if necessary by addition of sodium chloride and sterilised by filtration through a sterile filter using aseptic techniques before filling into suitable sterile vials or ampoules and sealing. Advantageously additives such as buffering, solubilising, stabilising, preservative or bactericidal or suspending and/or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The product is then freeze dried and the containers are sealed aseptically.

The dosage ranges for administration of the antibodies of the present invention are those to produce the desired therapeutic effect. It will be appreciated that the dosage range required depends on the precise nature of the antibody or composition, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Suitable daily dosages are in the range of 5-20 mg per kg of body weight. The unit dosage can vary from less than 100 mg, but typically will be in the region of 250-2000 mg per dose, which may be administered daily or less frequently (e.g. on alternative days for up to 1 week)

It is also within the scope of the invention to use the antibodies of the invention in therapeutic methods for the prevention or treatment of influenza virus infection in combination with one another, or as an adjunct to, or in conjunction with, other established therapies normally used in the prevention of treatment of influenza virus infection. For example, the antibodies of the present invention may be administered in conjunction with a suitable antiviral (e.g. OSELTAMAVIR™, RIMANTADINE™, ZANAMAVIR™, and/or AMANTADINE™).

The combination treatment may be carried out in any way as deemed necessary or convenient by the person skilled in the art and for the purpose of this specification, no limitations with regard to the order, amount, repetition or relative amount of the compounds to be used in combination is contemplated.

Definitions Section

An antibody that binds to an influenza virus of interest is one capable of binding said virus with sufficient affinity such that the antibody is useful as a therapeutic agent and/or vaccine potency reagent. By way of example, an antibody that binds to an influenza virus of interest is one that may bind to an influenza virus with an affinity ($K_a$) of at least $10^4$ M.

A therapeutically effective amount refers to the amount of the antibody, which when administered alone or in combination to a patient for treating or preventing influenza infection, or at least one of the clinical symptoms of influenza infection, is sufficient to affect such treatment or prevention of the disease, or symptom. The therapeutically effective amount can vary depending, for example, on the antibody, the infection, and/or symptoms of the infection, severity of the infection, and/or symptoms of the infection, the age, weight, and/or health of the patient to be treated, and the judgment of the prescribing physician. An appropriate therapeutically effective amount in any given instance may be ascertained by those skilled in the art or capable of determination by routine experimentation. A therapeutically effective amount is also one in which any toxic or detrimental effects of the antibody are outweighed by the beneficial effects.

A prophylactically effective amount is any amount of the antibody that, when administered alone or in combination to a patient, inhibits or delays the onset or reoccurrence of the influenza virus infection, or at least one of the clinical symptoms of influenza virus infection. In some embodiments, the prophylactically effective amount prevents the onset or reoccurrence of the influenza virus infection entirely. Inhibiting the onset means either lessening the likelihood of the infection's onset, or preventing the onset entirely.

For sequence comparison, typically one sequence acts as a reference sequence, to which test sequences may be compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Throughout this specification, reference to at least 80% sequence identity is used interchangeably with one or more of at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99 and/or 100% sequence identity.

Optimal alignment of sequences for comparison may be conducted, for example, by the local homology alignment algorithm of Smith and Waterman [Adv. Appl. Math. 2: 484 (1981)], by the algorithm of Needleman & Wunsch [J. Mol. Biol. 48: 443 (1970)] by the search for similarity method of Pearson & Lipman [Proc. Nat'l. Acad. Sci. USA 85: 2444 (1988)], by computer implementations of these algorithms (GAP, BESTFIT, FASTA, and TFASTA—Sequence Analysis Software Package of the Genetics Computer Group, University of Wisconsin Biotechnology Center, 1710 University Avenue, Madison, Vis. 53705), or by visual inspection [see Current Protocols in Molecular Biology, F. M. Ausbel et al, eds, Current Protocols, a joint venture between Greene Publishing Associates, In. And John Wiley & Sons, Inc. (1995 Supplement) Ausbubel].

Examples of algorithms suitable for determining percent sequence similarity are the BLAST and BLAST 2.0 algorithms [see Altschul (1990) J. Mol. Biol. 215: pp. 403-410; and "http://www.ncbi.nlm.nih.gov/" of the National Center for Biotechnology Information].

In a preferred homology comparison, the identity exists over a region of the sequences that is at least 5 contiguous amino acid residues, or at least 10 contiguous amino acid residues, or at least 15 contiguous amino acid residues, or at least 20 contiguous amino acid residues, or at least 25 contiguous amino acid residues, or at least 30 contiguous amino acid residues in length.

An "antibody" is used in the broadest sense and specifically covers antibodies and antibody fragments so long as they exhibit the desired biological activity. For example, an antibody is a protein including at least one or two, heavy (H) chain variable regions (abbreviated herein as VHC), and at least one or two light (L) chain variable regions (abbreviated herein as VLC). The VHC and VLC regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al, J. Mol. Biol. 196:901-917, 1987, which are incorporated herein by reference). Preferably, each VHC and VLC is composed of three CDRs and four FRs, arranged from amino-terminus to carboxy-terminus in the following order: FRI, CDRI, FR2, CDR2, FR3, CDR3, FR4.

The VHC or VLC chain of the antibody can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH2 and CH3, and optionally CH1. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

The term antibody, as used herein, also refers to a portion of an antibody that binds to an influenza virus, for example a molecule in which one or more immunoglobulin chains is not full length, but which binds to an influenza virus. Examples of binding portions encompassed within the term antibody include (i) a Fab fragment, a monovalent fragment consisting of the VLC, VHC, CL and CHI domains; (ii) a F(ab')$_2$ fragment, a bivalent fragment comprising two Fab fragments linked by a disulfide bridge at the hinge region; (iii) a Fc fragment consisting of the VHC and CHI domains; (iv) a Fv fragment consisting of the VLC and VHC domains of a single arm of an antibody, (v) a dAb fragment (Ward et al, Nature 341:544-546, 1989), which consists of a VHC domain; and (vi) an isolated complementarity determining region (CDR) having sufficient framework to bind, e.g. an antigen binding portion of a variable region. An antigen binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al. (1988) Science IAI-ATi-AIβ; and Huston et al. (1988) Proc. Natl. Acad. Sci USA 85:5879-5883). Such single chain antibodies are also encompassed within the term antibody. These are obtained using conventional techniques known to those with skill in the art, and the portions are screened for utility in the same manner as are intact antibodies.

Likewise, the term antibody embraces protein scaffolds.

Protein scaffolds provide universal binding frameworks to complement the expanding repertoire of therapeutic monoclonal antibodies and derivatives such as scFvs, Fab molecules, dAbs (single-domain antibodies), diabodies and minibodies. Scaffold systems create or modify known protein recognition domains either through creation of novel scaffolds or modification of known protein binding domains. Such scaffolds include but are not limited to:

(i) protein A based scaffolds—affibodies (Nord, K. et al 1997 "Binding proteins selected from combinatorial libraries of an alpha-helical bacterial receptor domain". Nat Biotechnol 15, 772-777);

(ii) lipocalin based scaffolds—anticalins (Skerra 2008 "Alternative binding proteins: anticalins—harnessing the structural plasticity of the lipocalin ligand pocket to engineer novel binding activities". FEBS J. 275:2677-83);

(iii) fibronectin based scaffolds—adnectin (Dineen et al 2008 "The Adnectin CT-322 is a novel VEGF receptor 2 inhibitor that decreases tumor burden in an orthotopic mouse model of pancreatic cancer". BMC Cancer 8:352);

(iv) avimers (Silverman et al 2005 "Multivalent avimer proteins evolved by exon shuffling of a family of human receptor domains". Nat Biotechnol 23:1556-61);

(v) ankyrin based scaffolds—darpins (Zahnd et al 2006 "Selection and characterization of Her2 binding-designed ankyrin repeat proteins". J Biol Chem. 281:35167-75); and (vi) centyrin scaffolds—based on a protein fold that has significant structural homology to Ig domains with loops that are analogous to CDRs. Ig domains are a common module in human proteins and have been widely applied as alternative scaffold proteins. Each of the above 'scaffold' publications is hereby incorporated (in its entirety) by reference thereto.

Reference to the term preventing or treating may be used synonymously with the term suppressing.

The amino acid sequences described herein may include one or more amino acid substitutions, deletions or additions. These changes are preferably of a minor nature, for example conservative amino acid substitutions (see below) and other substitutions that do not significantly affect the folding or activity of the antibody.

Conservative Amino Acid Substitutions
Basic: arginine
lysine
histidine
Acidic: glutamic acid
aspartic acid Polar: glutamine
asparagine
Hydrophobic: leucine
isoleucine
valine
Aromatic: phenylalanine
tryptophan
tyrosine
Small: glycine
alanine
serine
threonine
methionine In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for natural polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, β-naphthylalanine, β-pyridylalanine, N-guanidino-(butyl)-homoarginine, N, N'-guanidino-(dimethyl)-homoarginine, N, N'-guanidino-bis-(2,2,2,-trifluoroethyl)-homoarginine, N, N'-guanidino-(methyl, hexyl)-homoarginine, $N^e$-methyllysine, $N^e$-isopropyllysine, aminomethylphenylalanine, aminocyclohexylalanine, α-aminobutyric acid, 4-thiaproline, N-methylleucine, ornithine, norleucine, 5-bromo-tryptophan, 5-fluoro-tryptophan, 5-nitro-tryptophan, γ-aminobutyric acid, J-mercaptopropionyl, acetyl, pencillamine, and 4-fluorophenylalanine.

Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in *Xenopus* oocytes by microinjection of mutated mRNA and chemically aminoacylated suppressor tRNAs (Turcatti et al., J. Biol. Chem. 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

A number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related antibody sequences.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

| SEQ ID NOs |
|---|
| CDR3 (Kabat) |
| SEQ ID NO: 1 = STTTPPYEY |
| SEQ ID NO: 2 = RRDWRDY |
| SEQ ID NO: 3 = NPPGNLY |
| SEQ ID NO: 4 = DPLSTGWGQYSY |
| SEQ ID NO: 5 = STTTPPHEF |
| SEQ ID NO: 6 = RDGFFNRYDY |

|  SEQ ID NOs |
| --- |
| SEQ ID NO: 7 = SGPGGLNV |
| SEQ ID NO: 8 = TRWVPTMKADEYNY |
| SEQ ID NO: 9 = ASWVASLWSPSEYDY |
| SEQ ID NO: 10 = DPPGILY |
| SEQ ID NO: 11 = DPVCTAGWYRPSRFDL |
| SEQ ID NO: 12 = STLTPPHEY |
| SEQ ID NO: 13 = GNTGSSDRSSSYVH |
| SEQ ID NO: 14 = KSPLVDNEY |
| SEQ ID NO: 15 = KGFAPFLIGCPWGKAEYDY |
| SEQ ID NO: 16 = TKAFGIATITADYEL |
| SEQ ID NO: 17 = SSTVAPHEY |
| SEQ ID NO: 18 = SGPGGVEV |
| SEQ ID NO: 19 = SGPGGVIL |

CDR3 (IMGT)

| |
| --- |
| SEQ ID NO: 20 = KTSTTTPPYEY |
| SEQ ID NO: 21 = NTRRDWRDY |
| SEQ ID NO: 22 = NLNPPGNLY |
| SEQ ID NO: 23 = NADPLSTGWGQYSY |
| SEQ ID NO: 24 = KCSTTTPPHEF |
| SEQ ID NO: 25 = NARDGFFNRYDY |
| SEQ ID NO: 26 = MASGPGGLNV |
| SEQ ID NO: 27 = AGTRWVPTMKADEYNY |
| SEQ ID NO: 28 = AAASWVASLWSPSEYDY |
| SEQ ID NO: 29 = NLDPPGILY |
| SEQ ID NO: 30 = AADPVCTAGWYRPSRFDL |
| SEQ ID NO: 31 = KISTLTPPHEY |
| SEQ ID NO: 32 = GAGNTGSSDRSSSYVH |
| SEQ ID NO: 33 = HAKSPLVDNEY |
| SEQ ID NO: 34 = AVKGFAPFLIGCPWGKAEYDY |
| SEQ ID NO: 35 = AATKAFGIATITADYEL |
| SEQ ID NO: 36 = KFSSTVAPHEY |
| SEQ ID NO: 37 = KASGPGGVEV |
| SEQ ID NO: 38 = KASGPGGVIL |

CDR2 (Kabat)

| |
| --- |
| SEQ ID NO: 39 = VIGNYGNTNYADSVKR |
| SEQ ID NO: 40 = DIASTRGTTNYADSVKG |
| SEQ ID NO: 41 = GITYDDSTNYAGSVKG |
| SEQ ID NO: 42 = AITSGESTNYADSVKG |
| SEQ ID NO: 43 = VIGNYGNTNYADSVKG |
| SEQ ID NO: 44 = AVTTDGSTSYADYAKG |
| SEQ ID NO: 45 = VIGNGGNTNYAESVKG |
| SEQ ID NO: 46 = FITSTSAVTKYADSVKG |
| SEQ ID NO: 47 = CRASDGNTYYAESLKG |
| SEQ ID NO: 48 = SIAYDGSTSYADPVKG |
| SEQ ID NO: 49 = CISPSDSFTEYGDSVKG |
| SEQ ID NO: 50 = VIGNNDNTVYGDSVQG |
| SEQ ID NO: 51 = AIDWGDGPTTYADSVKG |
| SEQ ID NO: 52 = SIDGRGTPMYADSVKG |
| SEQ ID NO: 53 = CMNSRDGTTNYADSVKG |
| SEQ ID NO: 54 = AITAGGNTYYADSAKA |
| SEQ ID NO: 55 = VIGNYGNTNYADSVKG |
| SEQ ID NO: 56 = VIGNGGNTNYADSVKG |
| SEQ ID NO: 57 = VIGNGGTNYADSVKG |

CDR2 (IMGT)

| |
| --- |
| SEQ ID NO: 58 = IGNYGNT |
| SEQ ID NO: 59 = IASTRGTT |
| SEQ ID NO: 60 = ITYDDST |
| SEQ ID NO: 61 = ITSGEST |
| SEQ ID NO: 62 = IGNYGNT |
| SEQ ID NO: 63 = VTTDGST |
| SEQ ID NO: 64 = IGNGGNT |
| SEQ ID NO: 65 = ITSTSAVT |
| SEQ ID NO: 66 = RASDGNT |
| SEQ ID NO: 67 = IAYDGST |
| SEQ ID NO: 68 = ISPSDSFT |
| SEQ ID NO: 69 = IGNNDNT |
| SEQ ID NO: 70 = IDWGDGPT |
| SEQ ID NO: 71 = IDGRGTP |
| SEQ ID NO: 72 = MNSRDGTT |
| SEQ ID NO: 73 = ITAGGNT |
| SEQ ID NO: 74 = IGNYGNT |
| SEQ ID NO: 75 = IGNGGNT |
| SEQ ID NO: 76 = IGNGGNT |

CDR1 (Kabat)

| |
| --- |
| SEQ ID NO: 77 = IVTMG |
| SEQ ID NO: 78 = WYDVG |
| SEQ ID NO: 79 = RYRMG |
| SEQ ID NO: 80 = LYTMG |

| SEQ ID NOs |
|---|
| SEQ ID NO: 81 = IVTMG |
| SEQ ID NO: 82 = TYPMS |
| SEQ ID NO: 83 = FYTMG |
| SEQ ID NO: 84 = NYAIG |
| SEQ ID NO: 85 = GYAIA |
| SEQ ID NO: 86 = RYRMG |
| SEQ ID NO: 87 = AYAIA |
| SEQ ID NO: 88 = IITMG |
| SEQ ID NO: 89 = LYRVG |
| SEQ ID NO: 90 = MYMID |
| SEQ ID NO: 91 = NNAIG |
| SEQ ID NO: 92 = INAMG |
| SEQ ID NO: 93 = IVTMG |
| SEQ ID NO: 94 = FYTMG |
| SEQ ID NO: 95 = FYTMG |
| CDR1 (IMGT) |
| SEQ ID NO: 96 = GSISRIVT |
| SEQ ID NO: 97 = GFTFSWYD |
| SEQ ID NO: 98 = GSFFSRYR |
| SEQ ID NO: 99 = GSAFSLYT |
| SEQ ID NO: 100 = GSISRIVT |
| SEQ ID NO: 101 = GSAVLFSTYP |
| SEQ ID NO: 102 = NDIFSFYT |
| SEQ ID NO: 103 = GFSLDNYA |
| SEQ ID NO: 104 = GFPFDGYA |
| SEQ ID NO: 105 = GSFFSRYR |
| SEQ ID NO: 106 = GFTLGAYA |
| SEQ ID NO: 107 = GSMSRIIT |
| SEQ ID NO: 108 = VLTFSLYR |
| SEQ ID NO: 109 = GDIFVMYM |
| SEQ ID NO: 110 = GSTLNNNA |
| SEQ ID NO: 111 = GSAFSINA |
| SEQ ID NO: 112 = GSISSIVT |
| SEQ ID NO: 113 = DNIFSFYT |
| SEQ ID NO: 114 = TNIASFYT |
| Full length VHH |
| SEQ ID NO: 115 = QLQLVESGGGLVQPGGSLRLSCAASGSISRIVTMGWYRQASGKERELVAVI GNYGNTNYADSVKGRFTVSRDNAKDTAYLQMNGLNVEDTAIYYCKTSTTTP PYEYWGQGTQVTVSS |

| SEQ ID NOs |
|---|
| SEQ ID NO: 116 = QVQLVESGGGLVQPGGSLRLSCAASGFTFSWYDVGWYRRAPGKERELVADI ASTRGTTNYADSVKGRFTISRDNAKNSVYLQMNSLKPEDTAVYYCNTRRDW RDYWGQGIQVTVSS |
| SEQ ID NO: 117 = QVQLVESGGGLVQPGGSLRLSCAASGSFFSRYRMGWYRQAPGEORELVAGI TYDDSTNYAGSVKGRFTISRDNAKNTVHLQMNSLKPEDTAVYYCNLNPPGN LYWGQGTQVTVSS |
| SEQ ID NO: 118 = QVQLVESGGGLVQPGGSLRLCLASGSAFSLYTMGWYRQAPGNQRELVAAI TSGESTNYADSVKGRFTISRDNAKNTVYLQMNSLKPEDTAVYYCNADPLST GWGQYSYWGQGTQVTVSS |
| SEQ ID NO: 119 = QVQLVESGGGLVQPGGSLRLSCAASGSISRIVTMGVVYRQGPGKERELVAV IGNYGNTNYADSVKGRFTVSRDNAKDTAYLQMNNLNVEDTAMYYCKCSTTT PPHEFWGQGTQVTVSS |
| SEQ ID NO: 120 = QVQLVESGGGLVQPGGSLRLSCSASGSAVLFSTYPMSWYRQAPGKQRELVA AVTTDGSTSYADYAKGRFTISRDNAKNTVYLQMNSLKPEDTAVYYCNARDG FFNRYDYWGQGTQVTVSS |
| SEQ ID NO: 121 = QVQLVESGGGLVQPGGSLRLSCAASNDIFSFYTMGWYLQAIGKQREPVAVI GNGGNTNYAESVKGRFTISRDGAKNTAYLQMNSLKPEDTAVYYCMASGPGG LNVWGQGTQVTVSS |
| SEQ ID NO: 122 = QLQLVESGGGLVQPGGSLRLSCTASGFSLDNYAIGWFRRAPGEEREGVSFI TSTSAVTKYADSVKGRFTISRDNAKNTVYLQMTSLKPEDTAVYYCAGTRWV PTMKADEYNYWGQGTQVTVSS |
| SEQ ID NO: 123 = QLQLVESGGGLVQVGGSLRLSCAASGFPFDGYAIAWFRQAPGKEREGVSCR ASDGNTYYAESLKGRLTMSTDNAKNTVYLQMNSLKPEDTAVYYCAAASWVA SLWSPSEYDYWGQGTQVTVSS |
| SEQ ID NO: 124 = QVQLVESGGGLVQPGGSLRLSCAASGSFFSRYRMGWYRQAPGEQRELVASI AYDGSTSYADPVKGRFTISRDNANTVHLQMYSLKPDDTAVYYCNLDPPGIL YWGQGTQVTVSS |
| SEQ ID NO: 125 = QVQLVESGGGLVQPGGSLRLSCAASGFTLGAYAIAWFRQAPGKEREGVSCI SPSDSFTEYGDSVKGRFTVSRDNAKNTVYLQMNSLQPEDTAVYYCAADPVC TAGWYRPSRFDLWGQGTQVTVSS |
| SEQ ID NO: 126 = QVQLVESGGGLVQSGGSLRLSCAASGSMSRIITMGWYRQAPGMERELVAVI GNNDNTVYGDSVQGRFTVSRDNAKNTAYLQMNSLNAEDTAMYYCKISTLTP PHEYWGQGTQVTVSS |
| SEQ ID NO: 127 = QVQLVESGGGLVQAGDSLRLSCTASVLTFSLYRVGWFRQAPGKEREFVAAI DWGDGPTTYADSVKGRFTISRDNAERTAYLQINSLKPEDTAVYYCGAGNIG SSDRSSSYVHWGQGTQVIVSS |
| SEQ ID NO: 128 = QLQLVESGGGLVQPGGSLRLSCTASGDIFVMYMIDWYRQAPGKQRELVASI DGRGTPMYADSVKGRFTISRDNAKNTVYLQMNSLKPEDTAVYSCHAKSPLV DNEYWGQGTQVTVSS |
| SEQ ID NO: 129 = QLQLAESGGGLVQAGGSLRLSCAASGSTLNNNAIGWFRQAPGKEREGVSCM NSRDGTTNYADSVKGRFTISRDVAKNTVYLQMNSLKPEDTAVYFCAVKGFA PFLIGCPWGKAEYDYWGQGTQVTVSS |
| SEQ ID NO: 130 = QVQLVESGGGLVQPGGSLRLSCAASGSAFSINAMGWYRQAPGEEREFVAAI TAGGNTYYADSAKARFTISRDNAKNMLYLQMNSLKPEDTAMYYCAATKAFG IATITADYELWGQGTQVTVSS |

-continued

SEQ ID NOs

SEQ ID NO: 131 =
QVQLVESGGGLVQPGGSLRLSCSASGSISSIVTMGWYRQAPGKERELVAVI
GNYGNTNYADSVKGRFTVSRDNAKNTVYLQMNSLNVEDTAMYVCKFSSTVA
PHEYWGQGTQVTVSS

SEQ ID NO: 132 =
QVQLVESGGGLVQPGGSLRLSCAASDNIFSFYTMGWYRQSPGKERELVAVI
GNGGNTNYADSVKGRFTISRDNGKNKAHLQMNSLKPEDTAVYYCKASGPGG
VEVWGQGTQVTVSS

SEQ ID NO: 133 =
QVQLVESGGGLVQPGGSLRLSCAASTNIASFYTMGWYRQTPGQQRDVVAVI
GNGGNTNYADSVKGRFTISRDGAKNTAHLQMNSLKPEDTDVYYCKASGPGG
VILWGQGTQVTVSS

EXAMPLES

Example 1: Immunization Procedure and Analysis of Immune Response to Influenza Juvenile male alpacas were maintained at the Royal Veterinary College, Hertfordshire, UK. All animal experiments were performed in accordance with Home Office licence 80/2117. A blood sample prior to immunisation was obtained from the jugular vein and this was followed by 4 intramuscularly injections at 0 day, 21 day, 43 day and 71 day intervals divided between 4 legs. The primary immunisation consisted of 50 µg of recombinant H1 (A/California/07/09 (H1N1pdm) (Protein Sciences™) in 400 µl of sterile PBS and emulsified with 800 µl of complete Freunds adjuvant (Sigma) just prior to immunisation. Similarly three separate booster injections of 50 µg of recombinant H1 (A/California/07/09 (H1N1pdm) (Protein Sciences™) in incomplete Freunds adjuvant (Sigma) were administered. Approximately 3 days after each injection a 10 ml blood sample was collected from which serum was prepared after allowing the blood to clot overnight at 4° C. The serological response to A/California/07/09 at each stage of the immunisation schedule was evaluated by ELISA, haemagglutination inhibition assay (HI assay) on a panel of inactivated viral strains and microneutralisation assays (MN assays) using the pandemic H1N1 viral strain A/California/07/09 (Table 1). A clear response to the immunogen (H1N1 pdm) was seen which increased with each subsequent immunisation.

Example 2: Phage Displayed Single Domain VHH Antibody Library Construction

For antibody library construction approximately 10 ml samples of blood were collected from an immunized alpaca (Example 1) into heparin tubes. Peripheral blood lymphocytes were purified using a ficol hypaque centrifugation procedure (Sigma). RNA was extracted using RiboPure™ RNA extraction kit (Novagen) according to manufacturer's instructions and stored at −70° C. prior to cDNA synthesis. First strand cDNA synthesis was performed according to manufacturer's instructions (Invitrogen). In short, up to 200 ng of total RNA was used per oligo dT primed cDNA synthesis reaction which was allowed to proceed for 50 minutes at 50° C. after which time the reaction was terminated by incubation at 85° C. for 5 minutes followed by placing the reaction on ice. The reactions were collected by brief centrifugation and 1 µl of RNase H was added to each tube and incubated for 20 minutes at 37° C. The resulting cDNA was either stored at −20° C. or used immediately in primary PCR reaction to amplify antibody gene sequences.

Primary PCR was performed using two oligonucleotide primers designed to universally prime mammalian immunoglobulin genes in the CH2 domain and also at the 5' end of alpaca VHH genes (Harmsen et al., 2000) within the signal sequence. High Fidelity taq polymerase (Roche) was used for all DNA amplification.

Alp-CH2_Rev
5' CGC CAT CAA GGT ACC AGT TGA

AlpL-Fw_VHH
5' GGT GGT CCT GGC TGC

This resulted in the amplification of both a 600 bp and 900 bp antibody gene products. The 600 bp product corresponds to the heavy chain only antibody population and does not contain a CH1 domain. The 900 bp gene product corresponds to the conventional antibody heavy chain population and is not required. The 600 bp heavy chain only gene product was gel purified (QIAGEN) and then subjected to a secondary PCR step to amplify just the VHH antibody gene population (~450 bp) and to append appropriate restrictions sites for cloning into the phage display vector pNIBS-1 (Example 3). Primers for secondary PCR were designed to amplify all VHH genes by annealing to the antibody FR1 and FR4 regions. The Sfi1 and Not1 restriction sites were chosen for cloning as they do not cut frequently within antibody genes.

TABLE 1

Assessment of the serological immune response in immunised alpacas.

| | Immunisation strategy | | | HI titre[2] | | | | | MN titre[3] |
|---|---|---|---|---|---|---|---|---|---|
| Antigen | Immuni-zation | Bleed | Day | A/California/ 07/09 (H1N1) pdm | B/Brisbane/ 60/08 Control | A/Uruguay/ 716/07 (H3N2) | A/HongKong/ 213/03 (H5N1) | A/Vietnam/ 1194/04 (H5N1) | A/California/ 07/09 (H1N1) pdm |
| Rec HA[1] (H1) | Primary | Pre-immune | 0 | <8 | <8 | <8 | <8 | <8 | <10 |
| Rec HA (H1) | Boost 1 | First bleed | 21 | 64 | <8 | <8 | ND[4] | ND | ND |
| Rec HA (H1) | Boost 2 | Second bleed | 43 | 2048 | <8 | <8 | ND | ND | ND |
| Rec HA (H1) | Boost 3 | Third bleed | 71 | 8192 | <8 | <8 | <8 | <8 | >1280 |

[1]Rec HA (H1), recombinant haemagglutinin derived from A/California/07/09 pandemic H1N1 viral strain.
[2]HI titre, haemagglutination inhibition assay and titres are indicated as the reciprocal of the minimum serum dilution at which inhibition of agglutination of turkey erythrocytes is seen.
[3]MN titre, microneutralisation titre is given as the reciprocal of the minimum dilution at which lysis inhibition is seen of MDCK cells by influenza strain A/California/07/09 (H1N1 pdm).
[4]ND is not determined.

Alp_FR1_Sfi1
5' CTG CAG GGA TCC GTT AGC AAG GCC CAG CCG GCC ATG GCA CAG KTG CAG CTC GTG GAG TCN

Alp_FR4back_Not1
5' GCT AGT GCA TGG AGC TCA TGC GGC C

Approximately 5 µg of VHH antibody DNA was digested with Sfi1 restriction enzyme (New England Biolabs) in a 200 µl reaction overnight at 50° C. After further purification (QIAGEN) the VHH genes were digested with Not1 in a 100 µl reaction at 37° C. for 6 hours. The digested VHH genes were then ligated into the phage display vector pNIBS-1 (Example 3) which was similarly digested with Sfi1 and Not 1 restriction enzymes. Ligations were set up in a ratio of 4:1 insert to vector in a 20 µl reaction with each reaction containing approximately 100 ng of vector. After the addition of T4 DNA ligase (New England Biolabs) the reactions were incubated overnight at 16° C. The individual ligations were pooled and purified (QIAGEN) according to manufacturer's instructions. The purified ligation mix was then transformed into TG1 electrocompetent cells (Agilent) using electroporation (BIO-RAD). Cells were recovered from electroporation cuvettes using 1 ml SOC medium (Sigma) pre-warmed to 37° C. and then incubated at 37° C. for 1 hour with shaking to allow expression of antibiotic resistance. Libraries were spread on 22 cm dishes containing 2 TY agar ampicillin (100 µg/ml) and 20% v/v glucose. The library size was determined by preparing a dilution series counting viable colonies and was $5 \times 10^7$ independent clones. After overnight incubation of the 22 cm dishes at 37° C. the libraries were harvested by flooding the plates 2 TY agar carbenicillin (100 µg/ml), 20% v/v glucose and scraping off the colonies. The resuspended colonies representing the antibody library were then stored at −70° C. in 20% v/v glycerol.

Example 3: Construction of Phage Display Vector pN1BS-1

Figure 1B:
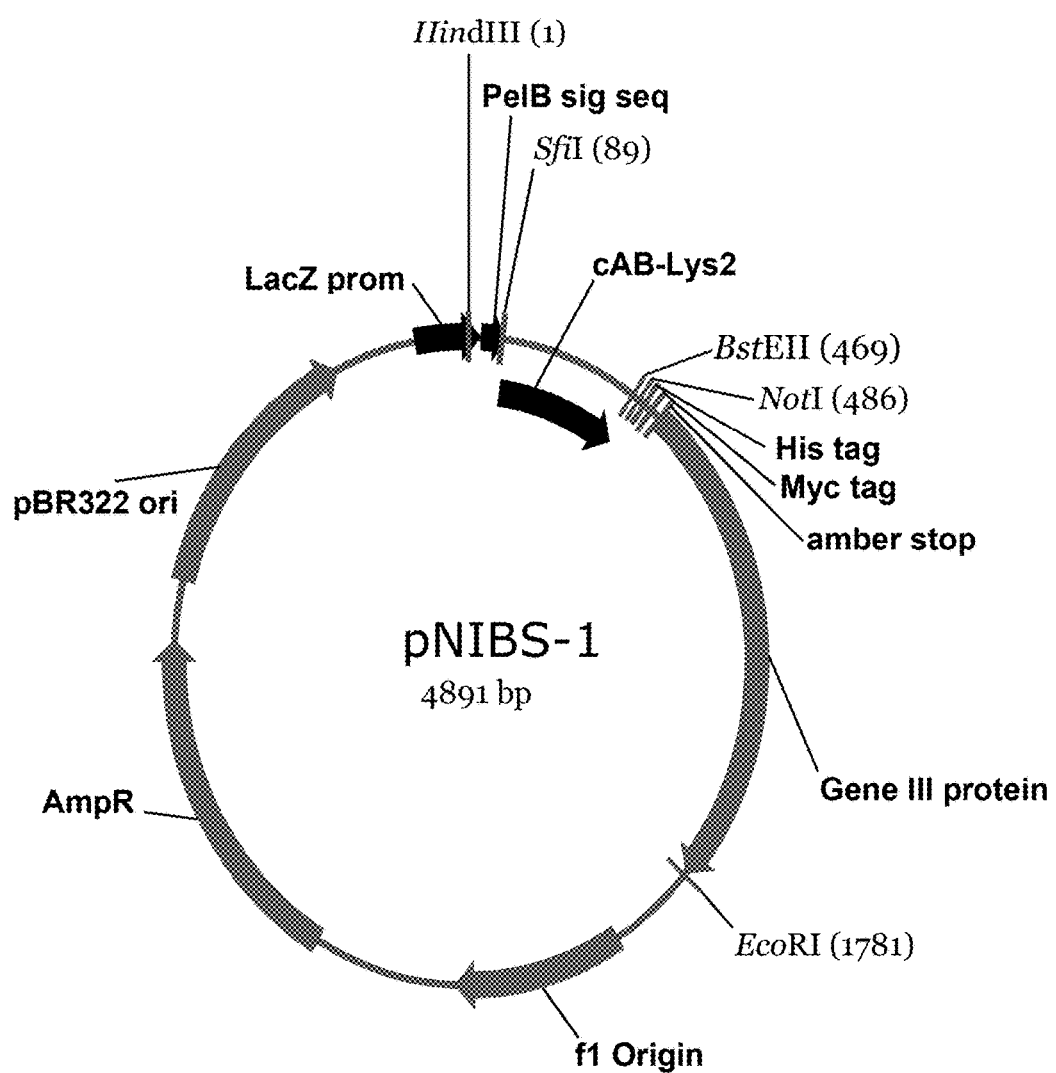
Figure 3A:
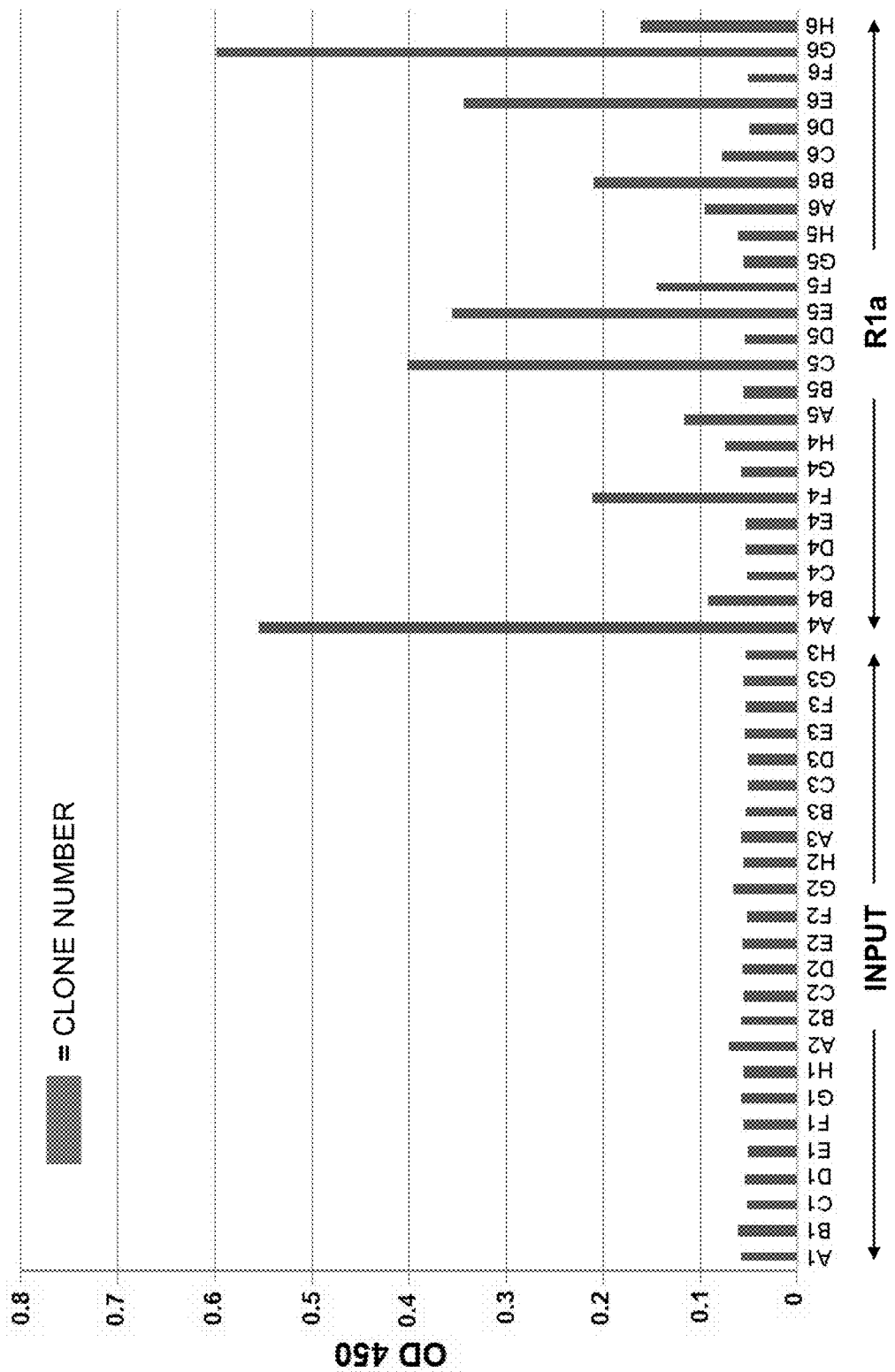
Figure 3B:
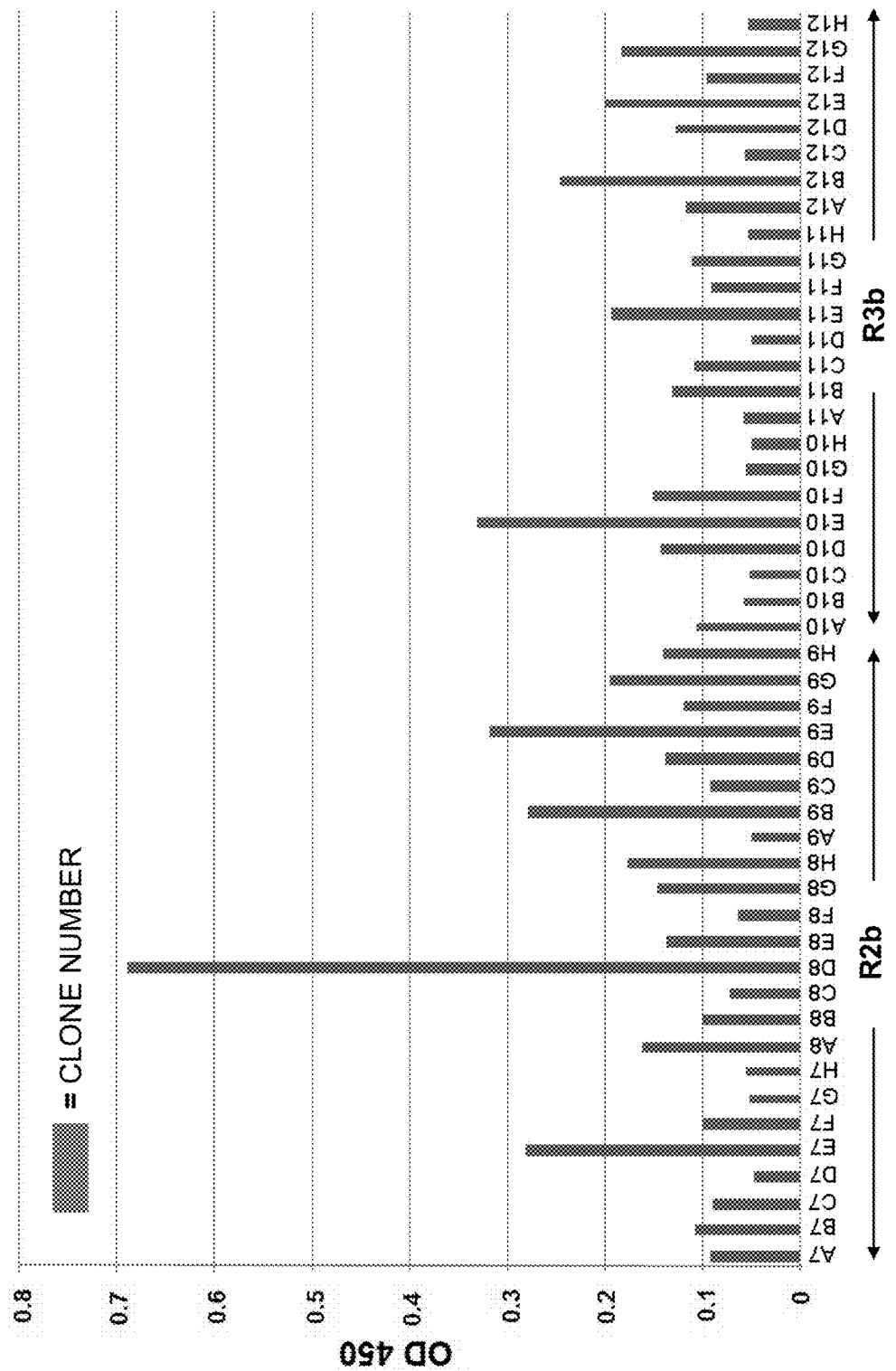

A polylinker sequence of 1782 bp was designed comprising the key features below:
(i) A pelB signal sequence which drives the secretion of expressed antibody into the periplasm and whose c terminal amino acid and DNA sequence is compatible with encoding a Sfi1 restriction site.
(ii) A hexa-histidine tag which is fused to the C-terminal end of a cloned VHH antibody and facilitates both purification and detection of expressed antibodies.
(iii) A c-Myc epitope tag attached to the C-terminal end of the cloned antibody after the hexa-histidine tag and facilitates detection of expressed antibody
(iv) Gene III sequence which encodes the M13 bacteriophage coat protein 3 and is in frame with antibody cassette to facilitate the production of antibody-gene III fusion products which can be displayed on the surface of phage.
(v) An amber DNA stop codon between the c-Myc epitope tag and the gene III phage coat protein. This codon is read as a stop codon in *Escherichia coli* but in strains carrying a mutant suppressor tRNA gene it is frequently read as an encoding amino acid and read through to produce a antibody-gene 3 fusion product. This allows display of the antibody-gene 3 fusion on phage. Suppression of the amber codon is generally of low efficiency and this has the advantage that soluble antibody not fused to gene 3 can be produced from the same *E. coli* clone cell without sub-cloning to remove the gene 3 sequence.
(vi) Sfi1 and Not1 restriction sites for cloning antibody genes were included as they cut infrequently in antibody genes and can be placed within DNA sequence whilst maintaining a functional expression cassette. Other restriction site like Mfe1 and BstEII were also incorporated as these are highly conserved in antibody germline genes and can be useful for cloning selected antibodies into other formats The polylinker sequence was synthesised from oligonucleotides (GENEART™) as a Hind111/EcoR1 fragment and cloned into the standard phagemid vector pUC119 to generate pNIBS-1 (FIG. 1A and FIG. 1B).

Example 4: Phage Antibody Library Selection Strategy

The phage displayed antibody library (Example 2) was inoculated into 50 mls of 2×TY media supplemented with carbenicillin at 100 µg/ml (w/v) and 2% v/v glucose (2×TY AG). An inoculation of greater than 10× library size was used to ensure library diversity is maintained during the phage rescue procedure [Library size $5 \times 10^7$ in size therefore $5 \times 10^8$ cells were used as a starter inoculation from a glycerol stock]. The culture was grown at 37° C. to an OD600 of 0.5 and 5 mls of culture (corresponding to approximately $7.5 \times 10^8$ bacteria) were transferred to a 50 ml sterile tube containing M13KO7 helper phage (New England Biolabs). The multiplicity of infection (MOI) was approximately 20:1 phage to bacteria so approximately $1.5 \times 10^{10}$ phage were used to infect the bacterial culture. After the bacterial culture was added to the appropriate amount of M13KO7 helper phage it was incubated in a water bath at 37° C. for 30 minutes. The infected cells were then centrifuged for 10 minutes at 4000×g, the supernatant removed and the bacterial pellet resuspended in 25 mls of pre-warmed 2×TY supplemented with 25 µg/ml kanamycin and 100 µg/ml ampicillin (2×TY AK) and incubated overnight at 30° C. with shaking. The next day cells were pelleted by centrifugation for 15 minutes at 4,000×g and the supernatant containing the phage displayed antibody library collected. To purify the phage 1/5 volume of 20% polyethylene glycol 6000, 2.5M NaCl (PEG) and incubated on ice for 1 hour. The phage were then pelleted in a microfuge and resuspended in 1 ml of sterile PBS. The remaining bacteria were then removed by a brief centrifugation and the phage supernatant transferred to a new tube. A second purification was performed by adding 200 µl of PEG and incubating on ice for 20 mins. The phage were collected by centrifugation for 5 minutes at 4° C. The pelleted phage were then resuspended in 1 ml sterile PBS and any further contaminating bacteria removed by a further brief centrifugation. The purified phage were then used for selection.

Phage antibody library selections were performed in immunotubes (Nunc) coated with 1 ml of 10 µg/ml recombinant haemagglutinin in PBS overnight at 4° C. [recombinant H1 [A/California/07/2009 (pandemic H1N1), recombinant H5 (A/Vietnam/1203/2004) protein Sciences™] (FIG. 2). The selection strategy was designed to recover both H1 specific antibodies and also H1/H5 cross reactive antibodies by alternating selection between immunotubes coated with H1 and H5 (FIG. 2). A parallel selection with an empty immunotube was also used to monitor antigen specific enrichment of the phage antibody library. The next day the immunotubes tube and control tube were blocked by filling completely with 2% w/v milk powder in sterile PBS (M-PBS) followed by a 2 hour incubation at room temperature. 500 µl of purified concentrated phage ($10^{12}$-$10^{13}$ phage) were added to 0.5 mls 4% MPBS and the phage blocked for 1 hour at room temperature. The immunotube was then washed with PBS Tween 20 (0.1% v/v) and 2×PBS and the phage mix transferred to the immunotubes covered with parafilm and incubated for 30 minutes on rotator and then 1.5 hours standing at room temperature. The immunotube was then washed 20 times with PBS Tween (0.1% v/v) and then 20 times with PBS [10 washes were used for the first round of selection to maximise the percentage recovery of antigen specific phage antibodies]. Specific phage antibodies were eluted by adding 1 ml of 100 mM triethylamine to the tube and covering with fresh parafilm followed by incubation for 10 min on rotator at room temperature. The eluted phage were then neutralised by transferring to a fresh microtube containing 0.5 ml 1M Tris HCl pH7.5. The eluted phage were then infected into E. coli to both prepare phage for a second round of selection and also to titrate the amount of phage recovered between sequential rounds of selection.

A culture of E. coli ER2378 cells was grown to an OD 600 of approximately 0.5. To amplify the selected phage for a next round of selection 1 ml of eluted phage were mixed with 5 mls of ER2738 culture and 4 mls of 2×TY media. This was then incubated in a water bath at 37° C. for 30 minutes. This was then spread onto 22 cm bioassay dishes 2×TY AG plus tetracycline (20 µg/ml) and grown overnight at 30° C. The bioassay dishes were then scraped and the recovered cells used for a second round of selection as above. In order to monitor the progress of selections between sequential round of selection the titre of input phage and output phage were determined. A serial dilution of phage were made in 500 µl 2TY to which 500 µl of log phage ER2738 culture was added and incubated in a water bath for 30 mins at 37° C. The infected cells were spread on 2×TY AG tetracycline (20 µg/ml) agar plates and the colonies counted after overnight incubation at 30° C. The phage titre before and after selection for three rounds was calculated as pfu/ml and showed an increase in the recovery of phage indicative of antigen selective enrichment of specific phage antibodies (Table 2).

TABLE 2

Selection and screening of phage displayed single domain antibody library

| Round | Antigen[1] | Input[2] Titre (pfu/ml) | Output[2] Titre (pfu/ml) | Number binders H5[3] | Number binders H1[3] |
|---|---|---|---|---|---|
| R1a | H1 | $2 \times 10^{13}$ | $5.6 \times 10^{8}$ | 5/24 | 10/24 |
| R2a | H1 | $4 \times 10^{13}$ | $4 \times 10^{10}$ | — | 12/24 |
| R2b | H5 | $4 \times 10^{13}$ | $2 \times 10^{10}$ | 16/24 | — |

TABLE 2-continued

Selection and screening of phage displayed single domain antibody library

| Round | Antigen[1] | Input[2] Titre (pfu/ml) | Output[2] Titre (pfu/ml) | Number binders H5[3] | Number binders H1[3] |
|---|---|---|---|---|---|
| R3a | H1 | $2.3 \times 10^{13}$ | $8 \times 10^{10}$ | — | 12/24 |
| R3b | H5 | $2.3 \times 10^{13}$ | $4.8 \times 10^{10}$ | 19/24 | — |

[1]recombinant antigen is either H1 derived from A/California/07/09 (H1N1 pdm) or H5 derived from A/Vietnam/1203/04 (H5N1)
[2]phage titres before and after selection are given as plaque forming units per ml (pfu/ml)
[3]number of antibodies binding to either recombinant H1(A/California/07/09) or recombinant H5 (A/Vietnam/1203/04) out of total number screened Example 5: Screening of Selected Library for Antibody Clones Binding to Recombinant H1 (A/California/07/09) and Recombinant H5 (A/Vietnam/1203/2004)

Primary screening of selected antibodies was done using unpurified soluble VHH antibodies induced in a 96 well format. Individual colonies from each round of selection were inoculated into 100 μl of 2×TY AG (2%) in 96 well flat bottom plate (Costar) using sterile toothpicks. The plates were incubated overnight at 30° C. rotating at 255 rpm. The next day 35 ml of 60% v/v glycerol was then added to each well and the master plate stored at −70° C. From this master plate a new 96 well round bottom plate (Costar) containing 120 μl of 2×TY ampicillin 0.1% w/v glucose was inoculated and grown for 6 hours at 37° C. until OD 600 is approximately 0.9. After which 30 μl 2×TY ampicillin 100 μg/ml plus 5 mM IPTG (1 mM final concentration) was added and continue shaking at 37° C. overnight. The plates were then centrifuged 600×g for 10 minutes and the supernatant containing soluble VHH antibodies was used to test antigen specific reactivity in ELISA.

A 96 well plate (Nunc) was coated with recombinant haemagglutinin at 1 μg/ml overnight in PBS at 4° C. The plates were washed three times with PBS and then blocked with 120 μl/well 2% w/v milk powder PBS (M-PBS) for 1 hour at room temperature. The plates were then washed twice each with PBS 0.1% (v/v) Tween and PBS. To each well 50 μl of 4% (w/v) milk powder PBS was added to each well and then 50 μl of culture supernatant containing soluble VHH. The ELISA plate was then incubated for 1.5 hours on a shaking platform at room temperature. After this incubation the plates were washed three times each with PBS 0.1% (v/v) Tween 20 and three times with PBS. To detect antibody binding 100 μl of anti myc 9E10-HRP (1/1000 dilution) (Roche) in 2% MPBS was added to each well and incubated for 1 hour at room temperature on a shaking platform. Plates were then washed three times each with PBS 0.1% (v/v) Tween 20 and three times with PBS and antibody binding developed using standard TMB staining. After stopping the reaction with 50 μl of 1M sulphuric acid the plates were read at 450 nM. An example of a primary ELISA screen using unpurified soluble VHH antibodies in a 96 well ELISA format is shown in FIG. 3A and FIG. 3B. Positive clones were scored as having at least twice background signal and were further characterised to analyse sequence diversity in particular the number of times a particular clone was recovered in the clones screened (Table 3). Using sequence analysis and evaluation by ELISA, nineteen antibodies with a unique VHH CDR3 sequence with specificity for recombinant H1 and/or recombinant H5 were isolated and progressed for more detailed secondary screening (Example 6).

TABLE 3

CDR sequences of unique antibodies specific to pandemic H1N1

| Clone[1] | SEQ ID[2] | Number [3] | $V_{HH}$ CDR1 [4] | $V_{HH}$ CDR2 [4] | $V_{HH}$ CDR3 [4] |
|---|---|---|---|---|---|
| R1a G5 | 1 | 4 | IVTMG | VIGNYGNTNYADSVKR | STTTPPYEY |
| R2b D8 | 2 | 2 | WYDVG | DIASTRGTTNYADSVKG | RRDWRDY |
| R2b E8 | 3 | 4 | RYRMG | GITYDDSTNYAGSVKG | NPPGNLY |
| R2b D9 | 4 | 1 | LYTMG | AITSGESTNYADSVKG | DPLSTGWGQYSY |
| R1a F4 | 5 | 2 | IVTMG | VIGNYGNTNYADSVKG | STTTPPHEF |
| R1a A5 | 6 | 34 | TYPMS | AVTTDGSTSYADYAKG | RDGFFNRYDY |
| R1a C5 | 7 | 1 | FYTMG | VIGNGGNTNYAESVKG | SGPGGLNV |
| R1a E5 | 8 | 3 | NYAIG | FITSTSAVTKYADSVKG | TRWVPTMKADEYNY |
| R1a F5 | 9 | 1 | GYAIA | CRASDGNTYYAESLKG | ASWVASLWSPSEYDY |
| R1a B6 | 10 | 1 | RYRMG | SIAYDGSTSYADPVKG | DPPGILY |
| R1a E6 | 11 | 1 | AYAIA | CISPSDSFTEYGDSVKG | DPVCTAGWYRPSRFDL |
| R1a G6 | 12 | 1 | IVTMG | VIGNNDNTVYGDSVQG | STTTPPYEY |
| R1a H6 | 13 | 1 | LYRVG | AIDWGDGPTTYADSVKG | GNTGSSDRSSSYVH |
| R2a E8 | 14 | 1 | MYMID | SIDGRGTPMYADSVKG | KSPLVDNEY |
| R2a G8 | 15 | 1 | NNAIG | CMNSRDGTTNYADSVKG | KGFAPFLIGCPWGKAEYDY |
| R2a B9 | 16 | 1 | INAMG | AITAGGNTYYADSAKA | TKAFGIATITADYEL |
| R2a F9 | 17 | 1 | IVTMG | VIGNYGNTNYADSVKG | SSTVAPHEY |
| R2a G9 | 18 | 1 | FYTMG | VIGNGGNTNYADSVKG | SGPGGVEV |
| R2a H9 | 19 | 1 | FYTMG | VIGNGGTNYADSVKG | SGPGGVIL |

[1]Clone identification number
[2]Sequence identification
[3] Number of times a particular CDR3 sequence appeared in screening of 62 independently isolated clones
[4] CDR defined according to Kabat numbering scheme

Example 6: Analysis of Purified Single Domain VHH Antibodies on Different Influenza Sub-Types For more detailed screening of antibody specificity, purified soluble VHH antibodies were purified from the *E. coli* periplasm. The nineteen different antibodies identified in Example 4 were each inoculated into into 2 ml of 2YT medium supplemented with 100 μg/ml (w/v) ampicillin, 2% (w/v) glucose, Tet (5 μg/ml) in a 10 ml tube and grown overnight at 37° C. with shaking. From this starter a 50 μl inoculation was taken into 50 mls of 2×TY medium supplemented with 100 μg/ml ampicillin, 0.1% (v/v) glucose and grown to an OD of ~0.6 at 37° C. Soluble antibody expression was induced with the addition of 1 mM IPTG followed by further incubation overnight at 30° C. The 50 ml culture was centrifuged for 20 minutes and the bacterial pellet re-suspended in 2.5 mls of periplasmic buffer (200 mM Tris HCl, pH 7.5, 20% (v/v) sucrose, 1 mM EDTA) followed by incubation on a rotator for 1 hour at 4° C. Cell debris was removed by centrifugation twice and the supernatant corresponding to the soluble VHH antibodies recovered from the bacterial periplasm were dialysed (Pierce) into PBS with two changes of buffer. After removal of EDTA by dialysis the antibody was purified by metal chelate chromatography (Clontech) according to manufacturer's instructions. Approximately 1 ml of purification resin was used per antibody. After incubation of the resin with the periplasmic preparations it was transferred to a gravity column (Biorad) and washed according to manufacturers instructions. The purified antibody was eluted into two bed volumes of elution buffer containing 100 mM imadazole. Antibody was further dialysed against PBS with two changes of buffer and antibody concentration determined using OD 280.

Inactivated viral preparations were reconstituted in 1 ml PBS and a 96 well ELISA plate was incubated overnight at 4° C. with 50 μl of antigen resuspended in 10 mls of 0.5M bicarbonate buffer pH9.6. Plates were washed and processed as in Example 4 except a serial dilution of purified antibody was used of 30, 10, 3, 1, 0.3, 0.1, 0.03, 0.01, 0.003, 0.001, 0.0003, 0.0001 μg/ml and assays were performed in duplicate. Dose response curves were plotted and EC50 values calculated using GraphPad Prism (Table 4). From this analysis cross-reactive antibodies were seen as R2b-E8, R2b-D9, R1a-A5, R1a-C5, R1a-B6, R1a-H6, and R2a-G8.

TABLE 4

Analysis of selected antibodies on different influenza viral strain sub-types

| Clone | A/California/7/2009 (H1N1) EC50[1] (µg/ml) | A/Brisbane/5 9/2007 (H1N1-like) EC50 (µg/ml) | A/Brisbane 10/2007 (H3N2) EC50 (µg/ml) | B/Brisbane/60/2008 EC50 (µg/ml) | A/TurkTurk/1/2005 (H5N1) EC50 (µg/ml) | A/Vietnam/1 19/2004 (H5N1) EC50 (µg/ml) | A/HongKong/213/2003 (H5N1) EC50 (µg/ml) | A/Indonesia/05/2005 (H5N1) EC50 (µg/ml) | A/Duck/Sing-Q/97 (H5N3) EC50 (µg/ml) | A/HongKong/1073/99 (H9N2) EC50 (µg/ml) | A/mallard/Eng/727/06 (H2N3) EC50 (µg/ml) |
|---|---|---|---|---|---|---|---|---|---|---|---|
| R1a-G5 | 1.73 | 0.29 | — | — | — | — | — | — | — | — | — |
| R2b-D8 | — | 14.8 | — | — | — | — | — | — | — | — | — |
| R2b-E8 | 3.64 | 18.4 | — | — | 0.89 | 1.83 | 1.2 | 0.80 | 4.98 | 5.63 | 0.002 |
| R2b-D9 | 0.90 | 0.80 | — | — | 0.76 | 1.81 | 2.8 | 0.58 | 5.64 | — | 0.06 |
| R1a-F4 | 0.79 | — | — | — | — | — | — | — | — | — | — |
| R1a-A5 | 0.31 | 0.38 | — | — | 0.13 | 0.25 | 0.27 | 0.15 | 0.27 | — | 0.006 |
| R1a-C5 | 1.71 | 3.30 | — | — | 0.15 | 2.89 | 2.9 | 1.17 | 7.57 | 4.48 | 0.06 |
| R1a-E5 | 3.23 | — | — | — | — | — | — | — | — | — | — |
| R1a-F5 | 0.55 | 0.70 | — | — | — | — | — | — | — | — | — |
| R1a-B6 | 0.39 | 0.58 | — | — | 0.44 | 0.82 | 0.37 | 0.42 | 1.32 | 2.3 | 0.102 |
| R1a-E6 | 2.46 | — | — | — | — | — | — | — | — | — | — |
| R1a-G6 | 0.30 | — | — | — | — | — | — | — | — | — | — |
| R1a-H6 | 3.85 | — | — | — | — | — | — | — | — | 5.7 | — |
| R2a-E8 | 0.51 | 1.42 | — | — | — | — | — | — | — | — | — |
| R2a-G8 | 4.11 | 1.86 | — | — | 1.93 | 3.36 | 6.2 | 5.7 | 9.67 | — | 2.5 |
| R2a-B9 | 1.00 | 9.84 | — | — | — | — | — | — | — | — | — |
| R2a-F9 | 0.19 | — | — | — | — | — | — | — | — | — | — |
| R2a-G9 | 0.30 | — | — | — | — | — | — | — | — | — | — |
| R2a-H9 | 0.97 | — | — | — | — | — | — | — | — | — | — |
| control | — | — | — | — | — | — | — | — | — | — | — |

[1]EC50 is the concentration of antibody in µg/ml which gives 50% of the maximal binding effect of each purified VHH single domain antibody on a representative group of viral sub-types using ELISA.
— No binding observed

Example 7: Affinity of Single Domain Antibodies on Recombinant Haemagglutinin from Different Influenza Viral Sub-Types Affinity of purified VHH antibodies (Example 5) was determined using the single cycle kinetics procedure on a BIAcore T100 machine (Karlsson et al., 2006). The procedure involves sequentially injecting an antibody concentration series over a haemagglutinin surface without regeneration between injections. Purified recombinant haemagglutinin of varying subtype (Protein Sciences, E enzymes) was immobilised onto a CM5 chip to approximately 3000 resonance units (RU). A series of antibody dilutions of 100 nM, 50 nM, 25 nM, 10 nM 5 nM were sequentially run over the different antigen surfaces without regeneration. A reference surface was subtracted prior to evaluation of the sensograms. Antibody affinity was determined using single cycle kinetics procedure of BIA evaluation software (GE healthcare) using a 1:1 fitting model (Table 5). Analysis on recombinant haemagglutinin and viral preparations (Example 6) showed antibodies R2b-E8, R2b-D9, R1a-A5, R1a-C5, R1a-B6, R1a-H6, and R2a-G8 to be cross-reactive antibodies.

TABLE 5

Binding analysis on different recombinant haemagglutinin using surface plasmon resonance

| Clone | SEQ ID | H1[a] (H1N1 pdm) Kd (nM) | H5[b] (H5N1) Kd (nM) | H2[c] (H2N2) Kd (nM) | H9[d] (H9N2) Kd (nM) | H3[e] (H3N2) Kd (nM) | H7[f] (H7N7) Kd (nM) |
|---|---|---|---|---|---|---|---|
| R1a-G5 | 1 | 24 | —[g] | — | — | — | — |
| R2b-D8 | 2 | —[g] | — | — | — | — | — |
| R2b-E8 | 3 | 8.2 | 3.6 | — | 87 | — | — |
| R2b-D9 | 4 | 0.4 | 1.6 | — | 59 | — | — |
| R1a-F4 | 5 | 7.3 | — | — | — | — | — |
| R1a-A5 | 6 | 3.3 | 0.7 | 186 | — | — | — |
| R1a-C5 | 7 | 1.9 | 2.7 | 67 | 22 | — | — |
| R1a-E5 | 8 | 0.6 | — | — | — | — | — |
| R1a-F5 | 9 | 9.2 | — | — | — | — | — |
| R1a-B6 | 10 | 0.7 | 1.7 | 43 | 7.6 | — | — |
| R1a-E6 | 11 | 22.8 | — | — | — | — | — |
| R1a-G6 | 12 | 4.4 | — | — | — | — | — |
| R1a-H6 | 13 | — | 241 | — | — | — | — |
| R2a-E8 | 14 | 0.8 | — | 34 | — | — | — |
| R2a-G8 | 15 | 3.1 | 9 | 39 | — | — | — |
| R2a-B9 | 16 | 0.2 | — | — | — | — | — |
| R2a-F9 | 17 | 60 | — | — | — | — | — |
| R2a-G9 | 18 | 62 | — | — | — | — | — |
| R2a-H9 | 19 | 2.8 | — | — | 40 | — | — |
| -control | | — | — | — | — | — | — |

[a]Single cycle affinity determination on full length recombinant H1 residues 18-530 derived from A/California/06/09. Affinity is given in nM to 1 decimal place and is the average of at least two separate assays.
[b]recombinant H5 A/Vietnam/1203/04 (H5N1)
[c]recombinant H2 A/Japan/305/1957 (H2N2)
[d]recombinant H9 A/HongKong/1073/99 (H9N2)
[e]recombinant H3 A/Brisbane/10/07 (H3N2)
[f]recombinant H7 A/Netherlands/219/03 (H7N7).
[g]— No Binding.

Example 8: Epitope Mapping

Evaluation of whether the antibodies bound to the globular head of haemagglutinin was evaluated in BIAcore. Recombinant haemagglutinin HA1 domain (18-344) (A/California/06/09) H1N1 and whole haemagglutinin (18-530) (E Enzymes) was immobilised on a CM5 BIAcore chip (GE Healthcare). Affinity was determined using a single cycle kinetics procedure (Example 7) and the cross-reactive antibodies were shown not bind to the globular head domain HA1 and by inference likely bind to the HA2 stalk region. The HA2 stalk region is more conserved across viral subtypes and as such is consistent with the cross-reactivity of these antibodies.

Further evidence localising cross-reactive antibodies to the more conserved haemagglutinin stalk region was obtained using an acid treatment which triggers an irreversible conformational change in the HA molecule. A viral preparation of H1N1 (A/California/06/09) was resuspended in 1 ml of PBS and 200 µl was diluted to 20 mls in PBS and the pH taken down to 2.83 with 1.5 mls of 1M HCl. After incubation for 2.5 hours at room temperature the antigen was neutralised with 20 mls of 0.5M bicarbonate buffer to give a final pH of ~9.0. This acid treated antigen was then used to coat ELISA plates overnight at 4° C. The next day ELISA plates were blocked and antigen binding was determined as in Example 6. A parallel assay with antigen that had not been treated with acid was also tested. All antibodies were shown to bind H1N1 which had not been treated with acid whereas several antibodies were shown to lose binding after including the cross-reactive antibodies R2b-E8, R2b-D9, R1a-A5, R1a-C5, R1a-B6, R1a-H6. Antibodies shown to bind to the globular head generally retained binding after acid treatment. This provided further evidence that the cross-reactive antibodies were binding to the more conserved stalk region of haemagglutinin.

Further evidence of cross reactive antibodies binding to the conserved stalk region was provided by assaying for the inhibition of heamagglutination of turkey erythrocytes. Heamagglutinin (HA) is the major viral coat protein which mediates binding to cell surface sialic acid via the globular head domain (HA1). Heamagglutination inhibition assays were performed as in Harmon et al., (1988) and were used to determine which antibodies could block attachment of influenza virus to turkey erythrocytes, and to indicate localisation of the antibody epitope to the globular head domain (HA1). Briefly serial dilutions of serum from immunised alpacas or purified VHH antibodies starting from 250 µg/ml were prepared. Serial dilutions were incubated with 8 HA units of virus per well and turkey erythrocytes were added to a concentration of 0.5% and the plate was incubated at room temperature for 30 minutes. All antibodies which showed binding to the globular head (HA1) domain were also positive for inhibition of haeamgglutination, except R2a-G8. Of all the H1/H5 cross neutralising antibodies identified only R1a-C5 showed any inhibition of heamagglutiniation (Table 6).

TABLE 6

Mapping of antibody epitopes to globular head or stalk region of haemagglutinin

| Clone | H1 (18-530)[1] (pdm H1N1) Kd (nM) | HA1 (18-344)[2] (pdm H1N1) Kd (nM) | HI titre (µg/ml) H1N1 (X-181)[3] | Acid treatment[4] | No acid treatment[4] |
|---|---|---|---|---|---|
| R1a-G5 | 24 | 26 | >1.56 | + | + |
| R2b-D8 | —[g] | — | >25 | + | + |
| R2b-E8 | 8.2 | — | >25 | − | + |
| R2b-D9 | 0.4 | — | >25 | − | + |
| R1a-F4 | 7.3 | 4.7 | >2.08 | + | + |
| R1a-A5 | 3.3 | — | >25 | − | + |
| R1a-C5 | 1.9 | 734 | >10.40 | − | + |
| R1a-E5 | 0.6 | — | >25 | − | + |
| R1a-F5 | 9.2 | 6.1 | >25 | ND | + |
| R1a-B6 | 0.7 | — | >25 | − | + |
| R1a-E6 | 22.8 | 36 | >25 | ND | + |
| R1a-G6 | 4.4 | 4.6 | >1.04 | + | + |
| R1a-H6 | — | — | >25 | − | + |
| R2a-E8 | 0.8 | — | >25 | − | + |
| R2a-G8 | 3.1 | 7.7 | >25 | ND[4] | + |
| R2a-B9 | 0.2 | — | >25 | − | + |
| R2a-F9 | 60 | 79 | >1.04 | + | + |
| R2a-G9 | 62 | 69 | >1.30 | + | + |
| R2a-H9 | 2.8 | 4.7 | >1.30 | + | + |
| -control | — | — | >25 | − | + |

[1] Single cycle affinity determination on full length recombinant H1 residues 18-530 from A/California/06/09. Affinity given to 1 decimal place in nM
[2] Single cycle affinity determination on globular head HA1 domain residues 18-344 from A/California/06/09. Affinity given to 1 decimal place in nM
[3] Haemagglutination inhibition (HI) assay was given as the minimum dilution of antibody at which inhibition of agglutination of turkey erythrocytes in µg/ml of purified antibody. Values are given as an average of three independent assays. Laboratory adapted H1N1 strain (X-181) was used
[4] ELISA on viral preparation of A/California/07/09 (H1N1 pdm) treated with acid and corresponding control with no acid treatment
[4] ND not determined Example 9—Humanisation of a $V_{HH}$ Antibody (Exemplified by Reference to Camelid Sequence VHH R2a-F9)

The framework regions (FR) of R2a-F9 were aligned with human germline sequence database using ClustalW and using sequences taken from V base (http://www.mrc-cpe.cam.ac.uk/vbase-ok)—see Table 7. The closest human germline sequence was DP53. The FR4 of R2a-F9 was aligned with the JH sequences and JH1 was chosen. The FR and CDR regions were defined according to Kabat et al., (1991). The IMGT numbering system (http://cines.fr) defines boundaries differently—for example cysteine 92 defines the start of CDR3 according to this nomenclature.

Framework residues in R2a-F9 different from germline VH-DP53 sequence are bold and underlined. The sequence identity in the framework regions is 79%. There are a total of 17 residues in the frameworks which are different between alpaca and human germline variable gene DP53.

The humanisation strategy involves replacing residues in FR that are not essential for antigen binding and stability. This involves choosing known typical camelid residues to be retained in the final sequence eg. 'Hallmark residues' (Vincke et al., 2008, Journal of Biological Chemistry, 284 (5), 3273-3284, which is hereby incorporated in its entirety by reference thereto). In R2a-F9 five hallmark residues have been identified 4 of which are in the FR2. A series of variants are made and the importance of each lama residue to antigen binding and stability is assessed.

All 12 constructs are tested in BIAcore for binding to H1, expression yield and thermal stability—see Table 8. Mutations to human germline which do not affect antigen binding are combined in a second round of constructs and the testing is repeated until a final humanised construct with the minimum amount of alpaca antibody sequence in the framework regions is obtained.

Combine all mutations that do not affect function and stability in final constructs to create an antibody gene with maximum human sequence content in the framework regions. A total of 13 alpaca residues are converted to human germline are shown in Table 9.

TABLE 7

```
              1                             30
R2a-F9-h  QVQLVESGGGLVQPGGSLRLSCSASGSISS
DP53      EVQLVESGGGLVQPGGSLPLSCAASGFTFS

CDR1- 3637            49 ------CDR2-------
          IVTMG  WYRQAPGKERELVA  VIGNYGN-TNYADSVKG
          SYWMH  WVRQAPGKGLVWVS  RINSDGSSTSYADSVKG

66
          RFTVSRDNAKNTVYLQMNSLNVEDTAMYY
          RFTISRNAKNTLYLQMNSLRAEDTAVYY

94 -CDR3----
R2a-F9-h  CKF SSTVAPHEY  WGQGTQVTVSS
DP53(96)  CAR ---------  WGQGTLVTVSS
```

TABLE 9

| R2a-F9 residue | Location | Hallmark diversity | VH-DP-53 germline | Comment |
| --- | --- | --- | --- | --- |
| Q1 | FR1 | — | E | Mutate Q1E |
| S23 | FR1 | — | A | Mutate S23A |
| S27 | FR1 | — | F | Mutate S27F |
| I28 | FR1 | — | T | Mutate I28T |
| S29 | FR1 | — | F | Mutate S29F |
| Y37 | FR2 | Yes (FYHILV) | V | Retain |
| E44 | FR2 | Yes (GEADQRSL) | G | Retain |
| R45 | FR2 | Yes (LRCILPQV) | L | Retain |
| E46 | FR2 | — | V | Mutate E46V |
| L47 | FR2 | Yes (WLFAGIMRS) | W | Retain |
| A49 | FR2 | — | S | Mutate A49S |
| V69 | FR3 | — | I | Mutate V69I |
| V78 | FR3 | — | L | Mutate V78L |
| N93 | FR3 | — | R | Mutate N93R |
| V94 | FR3 | — | A | Mutate V94A |
| M99 | FR3 | — | V | Mutate M99V |
| Q108 | FR4 | Yes (QLR) | L | Retain |

TABLE 8

First round Mutant constructs

R2a-F9_Q1E    QVQLVESGGGLVQPGGSLRLSCSASGSISS IVTMG WYRQAPGKERELVA
              VIGNYGNTNYADSVKG RFTVSRDNAKNTVYLQMNSLNVEDTAMYVCKF
              SSTVAPHEY WGQGTQVTVSS

R2a-F9_S23A   EVQLVESGGGLVQPGGSLRLSCAASGSISS IVTMG WYRQAPGKERELVA
              VIGNYGNTNYADSVKG RFTVSRDNAKNTVYLQMNSLNVEDTAMYVCKF
              SSTVAPHEY WGQGTQVTVSS

R2a-F9_S27F   EVQLVESGGGLVQPGGSLRLSCSASGFISS IVTMG WYRQAPGKERELVA
              VIGNYGNTNYADSVKG RFTVSRDNAKNTVYLQMNSLNVEDTAMYVCKF
              SSTVAPHEY WGQGTQVTVSS

R2a-F9_I28T   EVQLVESGGGLVQPGGSLRLSCSASGSTSS IVTMG WYRQAPGKERELVA
              VIGNYGNTNYADSVKG RFTVSRDNAKNTVYLQMNSLNVEDTAMYVCKF
              SSTVAPHEY WGQGTQVTVSS

R2a-F9_S29F   EVQLVESGGGLVQPGGSLRLSCSASGSIFS IVTMG WYRQAPGKERELVA
              VIGNYGNTNYADSVKG RFTVSRDNAKNTVYLQMNSLNVEDTAMYVCKF
              SSTVAPHEY WGQGTQVTVSS

R2a-F9_E46V   EVQLVESGGGLVQPGGSLRLSCSASGSISS IVTMG WYRQAPGKERVLVA
              VIGNYGNTNYADSVKG RFTVSRDNAKNTVYLQMNSLNVEDTAMYVCKF
              SSTVAPHEY WGQGTQVTVSS

R2a-F9_A49S   EVQLVESGGGLVQPGGSLRLSCSASGSISS IVTMG WYRQAPGKERELVS
              VIGNYGNTNYADSVKG RFTVSRDNAKNTVYLQMNSLNVEDTAMYVCKF
              SSTVAPHEY WGQGTQVTVSS

R2a-F9_V69I   EVQLVESGGGLVQPGGSLRLSCSASGSISS IVTMG WYRQAPGKERELVA
              VIGNYGNTNYADSVKG RFTISRDNAKNTVYLQMNSLNVEDTAMYVCKF
              SSTVAPHEY WGQGTQVTVSS

R2a-F9_N93R   EVQLVESGGGLVQPGGSLRLSCSASGSISS IVTMG WYRQAPGKERELVA
              VIGNYGNTNYADSVKG RFTVSRDNAKNTLYLQMNSLNVEDTAMYVCKF
              SSTVAPHEY WGQGTQVTVSS

R2a-F9_V94A   EVQLVESGGGLVQPGGSLRLSCSASGSISS IVTMG WYRQAPGKERELVA
              VIGNYGNTNYADSVKG RFTVSRDNAKNTVYLQMNSLRVEDTAMYVCKF
              SSTVAPHEY WGQGTQVTVSS

R2a-F9_M99V   EVQLVESGGGLVQPGGSLRLSCSASGSISS IVTMG WYRQAPGKERELVA
              VIGNYGNTNYADSVKG RFTVSRDNAKNTVYLQMNSLNAEDTAMYVCKF
              SSTVAPHEY WGQGTQVTVSS

R2a-F9_M99V   EVQLVESGGGLVQPGGSLRLSCSASGSISS IVTMG WYRQAPGKERELVA
              VIGNYGNTNYADSVKG RFTVSRDNAKNTVYLQMNSLNVEDTAVYVCKF
              SSTVAPHEY WGQGTQVTVSS

Example 10: Introduction of a CDR3 VHH Sequence into a Human Antibody

As the VHH CDR3 is the key determinant of binding specificity, this loop may be readily incorporated into an entirely human VH gene whilst preserving functionality. The resulting antibody is entirely human with a human CDR1 and CDR2 except for the VHH CDR3 loop which is derived from alpaca. Such an antibody has a lower risk of eliciting an adverse immune response when administered as a therapeutic monoclonal antibody due to the increased content of human sequence as compared to the antibody derived in Example 9.

By way of example, the VHH CDR3 loop is grafted into an appropriate human V gene by designing an oligonucleotide corresponding to the VHH CDR3 sequence bracketed by human antibody germline sequence corresponding to FR3 and FR4 of either an individual human VH or a collection of human VH sequences. An example is shown below which includes a 3' oligonucleotide corresponding to the VHH-CDR3 of R2a-F9 (SEQ ID 36) appended with a degenerate sequence designed to prime to all human VH3 gene family members. The VH3 gene was selected simply because camelid VHH antibodies show greatest homology to the human VH3 family. The corresponding 5' primer is a degenerate oligonucleotide designed to anneal to the FR1 of all human VH3 gene members. These two oligonucleotides are used in a PCR reaction with human VH genes derived from cDNA prepared for example from peripheral blood lymphocytes of naive donors using established methods. The design shown below appends Sfi1 and BstEII restriction sites to facilitate cloning into the phage display vector pNIBS-1 (Example 3).

```
GGCCCAGCCGGCC ATG GCA SAR GTG CAG CTG KTG GAG
    Sfi1               FR1(Human VH3)

K    F
 ▶-----◀  CTG TRB CGR MAY ATA RTG ACA TTC AAA
             FR3(Human VH3)

S   S   T   V   A   P   H   E   Y   W   G   Q   G
  AGT TCA TGG CAA CGC GGC GTG CTC ATG ACC CCG GTC CCT
                      VHH CDR3

T    Q   V   T
  TGG GTC CAG TGG
       BstEII
```

After construction of a phage display library of human VH genes grafted with the VHH-CDR3 of R2a-F9, the library is then selected on recombinant H1 as in Example 4 and humanised antibodies screened as in Example 5.

Example 11: Assessment of Efficacy In Vivo

The efficacy of cross-reactive antibodies for passive immunotherapy is assessed in a mouse challenge model. The seven H1/H5 cross neutralising antibodies (R2b-E8, R2b-D9, R1a-A5, R1a-C5, R1a-B6, R1a-H6, R2a-G8) are tested for their ability to protect BALB/c mice from challenge with H1N1 (A/California/07/09) and H5N1 (A/Vietnam/1203/2004) virus in a prophylactic setting. VHH antibodies are expressed, purified (Example 6) and administered intranasally as monovalent agents at 5 mg/kg, 24 hours before challenge with a lethal dose of virus. A non-relevant VHH antibody and a PBS only arm of the study are included as controls. Survival, body weight and viral titres in lung and other tissues are monitored to assess the antibodies' ability to protect against lethal challenge with H1N1 and H5N1 virus. Said antibodies demonstrate protection against such lethal challenge. Antibodies are also evaluated in a therapeutic setting where antibody is administered 24 hours post-infection with H1N1 and H5N1. Again survival, body weight and post challenge viral titres in lung and other tissues are monitored. Said antibodies demonstrate protection against such lethal challenge.

Example 12: Neutralisation Activity of Recombinant VHH Antibodies on H1N1 and H5N1

The influenza microneutralisation assay was performed essentially as in Harmon et al., (1988). In brief, either serum from a immunised alpaca or purified VHH antibodies (at a starting concentration of 5 µg/ml) were serially diluted, two-fold, in a 50 µl volume of assay diluent (DMEM with the addition of; 2 mM glutamine, Pen/Strep 1/100, Amphotericin 1/100, non-essential amino acids and FCS 1/200) in a 96 well flat bottom plate (Costar) in duplicate columns 1-10. The reverse genetics reassortants NIBRG-14 (A/Vietnam/1194/04; H5N1) and the reassorted attenuated virus X-181 (A/California/07/09;H1N1) were used in viral neutralisation assays. X-181 virus and NIBRG-14 viruses were used at $10^2 TCID_{50}$ virus dose per 50 µl of assay diluents. In all assays a 'virus only' (VC) control and a 'cells only' (CC) control was included. Plates were incubated at room temperature for 1 hour and 100 µl of $1.5 \times 10^5$/ml MDCK cells (Madin-Darby canine kidney cells) was added to all wells. Plates were incubated for 18 hours at 30° C. in 5% $CO_2$. Cells were fixed with 100 µl of 0.6% w/v methanol/hydrogen peroxide per well and left for 20 minutes at room temperature. Plates were then washed 3 times in PBS Tween-20 (0.05% w/v). Growth of influenza virus and release of nucleoprotein was with a primary anti-influenza A nucleoprotein (Serotec) mouse monoclonal antibody. 100 µl of this antibody was added to each well at a 1:3000 dilution in 6 salt PBS/Tween-20 (0.1%) 5% w/v Marvel milk. 100 µl of this was added to all wells and plates and incubated for 1 hour at 37° C. Rabbit anti-mouse IgG polyclonal HRP conjugate (DAKO) at a dilution of 1:5000 in 6 salt PBS/Tween-20 (0.1% v/v), 5% (w/v) Marvel milk powder, 1% (v/v) bovine serum albumin was used and incubated for 1 hour at 37° C. Plates were washed 4 times and developed using TMB staining. The reactions were stopped by the addition of 100 µl of 0.5M HCl to each well and read at 450 nm & 620 nm. The 620 nm values were subtracted from the 450 nm values to correct for plate absorption. The antibody concentration at which 50% viral neutralisation was seen was determined using the equation;

$$\frac{(\text{mean } OD \text{ of } VC) - (\text{mean } OD \text{ of } CC)}{2} + (\text{mean } OD \text{ of } CC) = x$$

Where x is the OD at which 50% of MDCK cells were infected.

All antibody clones except R2b-D8, R1a-F4, R1a-E5, R1a-F5, and R1a-E6 were able to neutralise X-181 which is a laboratory adapted strain of H1N1 (Table 10). Of the H1N1 neutralising antibodies, R2b-E8, R2b-D9, R1a-A5, R1a-C5, R1a-B6, R1a-H6 and R2a-G8 were also able to neutralise NIBRG-14 (H5N1) and were deemed to be cross neutralising antibodies (Table 10). This was consistent with the cross reactivity data shown in examples 5, 6 and 7. For antibodies R2b-E8, R2b-D9, R1a-A5, R1a-B6 and R1a-H6 this was consistent with absence of haemagglutination inhibition activity and specificity for acid sensitive epitopes in the conserved stalk region of haemagglutinin (Table 6).

TABLE 10

Antibody neutralisation of H1N1 and H5N1 viral infection of MDCK cells

| Clone | Neutralisation X-181 A/California/07/09 (H1N1 pdm) EC50 nM | Neutralisation NIBRG-14 A/Vietnam/1194/04 (H5N1) EC50 nM |
|---|---|---|
| R1a-G5 | 30 nM | — |
| R2b-D8 | — | — |
| R2b-E8 | 54 nM | 29 nM |
| R2b-D9 | 55 nM | 7.8 nM |
| R1a-F4 | — | — |
| R1a-A5 | 23 nM | 8.0 nM |
| R1a-C5 | 23 nM | 55 nM |
| R1a-E5 | — | — |
| R1a-F5 | — | — |
| R1a-B6 | 31 nM | 20 nM |
| R1a-E6 | — | — |
| R1a-G6 | 12 nM | — |
| R1a-H6 | 53 nM | 12 nM |
| R2a-E8 | 26 nM | — |
| R2a-G8 | 538 nM | >1 µM |
| R2a-B9 | 29 nM | — |
| R2a-F9 | 68 nM | — |
| R2a-G9 | 62 nM | — |
| R2a-H9 | 16 nM | — |
| control | — | — |

Example 13: Evaluation as a 'Universal Antibody' for Vaccine Potency

Cross-reactive antibodies of the invention are used in potency assays for attenuated influenza vaccines. The cross-reactive antibodies of this application cross-react with (1) many/all haemagglutinins of one subtype/type of influenza virus, or with (2) haemagglutinins of more than one subtype of influenza A virus with all of these subtypes belonging to one of the two recognised phylogenetic groups of influenza HA, or with (3) HAs from both phylogenetic groups, group 1 and group 2.

An antibody having cross-reactivity as in (1) is useful for the potency testing of multivalent, preferably trivalent and quadrivalent, influenza vaccines. An antibody having cross-reactivity as in (2) is useful for the potency testing of multivalent, preferably trivalent and quadrivalent, influenza vaccines; for the potency testing of pandemic or pre-pandemic influenza vaccines containing a single subtype of influenza A virus; and for the potency testing of vaccines containing more than one subtype/type, with each virus component belonging to a different phylogenetic group. An antibody having cross-reactivity as in (3) is useful for the potency testing of monovalent influenza vaccines, preferable pandemic and pre-pandemic influenza vaccines.

The use of such cross-reactive antibodies in potency testing eliminates the need to frequently change the antibody reagent as is the case in currently used methods, for which specific sheep antisera have to be generated every time a strain change is announced and implemented; production of a new antiserum for every antigenically drifted virus that is used in influenza vaccines has been identified as a potential bottleneck in the pathway from virus strain change to vaccination with an updated influenza vaccine. To solve this problem, cross-reactive antibodies of this invention are produced in advance and are therefore available at all times; following a strain change in influenza vaccine production, (a) cross-reactive antibody/antibodies can be used immediately, with no lead time to availability of strain-specific antibodies.

By way of example, a cross-reactive antibody is used in the single radial immunodiffusion (SRID or SRD) assay. Following standard protocols for SRD, the cross-reactive antibody is incorporated into a gel matrix and then used in the assay. A precipitin ring is formed when influenza haemagglutinin is allowed to diffuse into the gel and can be measured following standard protocols for visualisation of the SRD ring/zone.

In another example, cross-reactive antibodies are used in ELISA assays to quantitatively measure the potency of vaccines and pre-vaccine samples, such as monovalent bulks. ELISA assays of various formats may be used. For instance, a sandwich ELISA using an antibody coated on a solid surface to capture haemagglutinin and an antibody to detect captured HA may be used. The capture and the detection antibody may be the same antibody, or may be different antibodies. Either of the two antibodies, or both, may be cross-reactive antibodies of this invention. In another format, a competition ELISA is used. HA is coated on a solid surface and reacted with cross-reactive antibody/ antibodies of this invention. A reference antigen, or the sample to be measured, is used as a competitive reagent. Reduction of binding of the cross-reactive antibody to the coated HA can be used to quantify HA in solution, using a standard curve generated from the reference antigen reagent. Other formats of ELISAs may be employed to a similar effect; in all cases, a cross-reactive antibody, or a multitude of cross-reactive antibodies, are used as specific reagents to capture and/or detect HA.

In another example, Surface Plasmon Resonance (SPR) technology is used to establish a potency assay for attenuated influenza vaccines. Cross-reactive antibodies are used to detect and quantify HA protein/antigen. Various formats of SPR-based assays may be used. In a preferred embodiment, a competitive assay, with reference antigen and cross-reactive antibody competing for binding to HA coated on a chip, as appropriate for the specific device used, is employed.

In another example, cross-reactive antibody/antibodies are used in a method using proteins (in particular, HA) immobilised on a membrane. The membrane may be a nitrocellulose membrane, a PVDF membrane, or another suitable membrane. Immobilisation of protein and HA on the membrane may occur through various processes, such as Western Blotting using various devices, slot blotting, spotting onto membrane, and others.

In another example, cross-reactive antibodies are used to enrich HA from samples, such as vaccines or monovalent bulks. Enrichment may be through use of cross-reactive antibodies in immune-precipitation, affinity chromatography, magnetic separation (with antibody being coupled by some means to magnetic substances, such as paramagnetic beads), or any other immunological method capable of binding and enriching HA out of a sample which will be, for the most part, a liquid containing HA in solution. HA adsorbed to substances, such as adjuvants, may also be subjected to such enrichment, either in untreated samples or following treatment to de-adsorb the HA. Enriched HA may then be quantified using any suitable method. Suitable methods include, but are not limited to, mass-spectrometry, in particular isotope dilution mass spectrometry as used in 'immunocapture isotope dilution mass spectrometry' (Pierce et al., Analytical Chemistry, 2011 dx.doi.org/10.1021/ac2006526) and HPLC.

Example 14: Design of an Influenza Vaccine which Elicits a Cross-Protective Immune Response Against Future Group 1 Influenza Strains Cross-reactive antibodies are used to define epitopes on haemagglutinin, which are structurally conserved across different viral subtypes. Such epitopes are then used to design a vaccine, which when administered to patients elicits a protective immune response against future viral subtypes so eliminating the need for repeated seasonal vaccination against a constantly evolving influenza virus.

Mapping the epitope of a cross-reactive antibody of this invention is performed by co-crystallisation of the cross-reactive antibody in complex with haemagglutinin and subsequent X-ray crystallography. Alternatively, the cross-reactive antibody is constructed as a gene fragment phage display library derived from the HA gene of an influenza virus such as a pandemic H1N1 (e.g. A/California/07/2009). The H1-HA gene is synthesised, digested with DNAase into fragments and cloned into the phage display vector pNIBS-1. This gene fragment phage-displayed library is then selected with purified cross-reactive single domain antibodies described in this invention. Sequence analysis of the selected gene fragments is then used to delineate the cross-neutralising epitope(s) and map them against available HA sequences in the public databases to determine the extent of conservation across all 16 HA subtypes. For more 'fine-tuned' epitope mapping, alanine scanning mutagenesis of the HA gene fragment displayed on phage is used followed by screening for loss of specific antibody binding whilst preserving display on phage. The minimal haemagglutinin gene fragment which can generate a correctly folded product corresponding to the cross-reactive antibody epitope is then expressed and purified in a heterologous gene expression system or synthesised as a peptide using established chemical procedures. This recombinant HA epitope is then used to immunise BALB/c mice and to protect from lethal challenge with different viral strains including H5N1 and H1N1 viral sub-types.

Alternatively, the cross-reactive antibodies of the invention can be used to isolate anti-idiotypic antibodies which represent a structural mimic of the relevant cross-reactive epitope on haemagglutinin. Such anti-idiotypic antibodies when used as a vaccine elicit an immune response which cross-reacts with relevant epitopes on viral haemagglutinin. An advantage of using the single domain VHH antibodies described in this invention is that they are structurally much simpler than a conventional antibody, which requires the stable association of both a VH and VL domain to form the paratope. By way of example, a cross-reactive single domain antibody (e.g. R1a-B6) is used to immunise an alpaca as in Example 1 and a phage display antibody library is constructed as in Example 2. The library is then selected on the initial cross-reactive antibody used for immunisations (Example 4). Anti-idiotypic antibodies are described as those which bind to the cross-reactive antibody (R1a-B6) used for immunisation and are negative for other antibodies carrying different CDR1, CDR2 and CDR3 sequences but having similar framework regions.

---

The invention claimed is:

1. A composition, comprising a single domain camelid antibody, wherein said single domain antibody comprises a CDR3 amino acid sequence selected from SEQ ID NOS: 1-38.

2. The composition of claim 1, wherein said single domain camelid antibody demonstrates antigenic cross-reactivity to HI and H5 influenza virus subtypes.

3. The composition of claim 1, wherein said single domain camelid antibody demonstrates antigenic cross-reactivity to H2 and H9 influenza virus subtypes.

4. The composition of claim 1, wherein said single domain camelid antibody demonstrates antigenic cross-reactivity to one or all of H2, H5, H6, H9, HI 1, H13, H16, H8, and H12 influenza virus subtypes.

5. The composition of claim 1, wherein said-single domain camelid antibody further comprises a CDR2 amino acid sequence selected from SEQ ID NOS: 39-76.

6. The composition of claim 1, wherein said single domain camelid antibody further comprises a CDR1 amino acid sequence selected from SEQ ID NOs: 77-114.

7. The composition of claim 1, wherein said single domain camelid antibody comprises an amino acid sequence selected from SEQ ID NOS: 115-133.

8. A composition comprising two or three or four or more covalently linked single domain camelid antibodies, wherein said two or three or four or more single domain camelid antibodies are the same or different, and each comprises a CDR3 amino acid sequence selected from SEQ ID NOs: 1-38.

9. The composition of claim 1, wherein said single domain camelid antibody comprises a humanized framework region.

10. A composition comprising a single domain camelid antibody, wherein said single domain antibody comprises one or more covalently linked CDR3 $V_{HH}$ amino acid sequence, each selected from SEQ ID NOs: 1-38.

11. The composition of claim 1, wherein said single domain camelid antibody lacks one or more human Vhh amino acid sequence, and in place thereof consists or comprises one or more covalently linked CDR3 VHh amino acid sequence, each selected from SEQ ID NOs: 1-38.

12. The composition of claim 1, wherein said single domain camelid antibody demonstrates neutralising activity against a HI (e.g. H1N1) influenza virus, for example against strain A/California/06/09 and/or A/California/7/2009 and/or A/Brisbane/59/2007.

13. The composition of claim 1, wherein said single domain camelid antibody demonstrates neutralising activity against a H5 (e.g. H5N1 or H5N3) influenza virus, for example against strain A/Vietnam/1203/2004 and/or A/Vietnam/1194/04 and/or A/Vietnam/119/2004 and/or HongKong/213/2003 and/or A/turkey/Turkey/1/2005 and/or A/Indonesia/05/2005 and/or A/Duck/Singapore-Q/119-3/97.

14. The composition of claim 1, wherein said single domain camelid antibody demonstrates neutralising activity against a H2 influenza virus (e.g. H2N2 or H2N3), for example against strain A/Japan/305/1957 and/or A/Mallard/Eng/727/06.

15. The composition of claim 1, wherein said single domain camelid antibody demonstrates neutralising activity against a H9 influenza virus (e.g. H9N2), for example against strain A/HongKong/1073/99.

16. The composition of claim 1, wherein said single domain camelid antibody demonstrates neutralising activity against one, or more, or all Group I haemagglutinin influenza viruses selected from the group consisting of HI, H2, H5, H6, HI 1, H13, H16, H9, H8 and/or H12 influenza viruses.

* * * * *